US008412315B2

(12) United States Patent
Ross

(10) Patent No.: US 8,412,315 B2
(45) Date of Patent: *Apr. 2, 2013

(54) ANALYSIS OF HEART RATE VARIABILITY DATA IN ANIMALS FOR HEALTH CONDITIONS ASSESSMENT

(75) Inventor: Christine Ross, Rancho Santa Fe, CA (US)

(73) Assignee: Christine Ross, Rancho Santa Fe, CA (US)

( * ) Notice: Subject to any disclaimer, the term of this patent is extended or adjusted under 35 U.S.C. 154(b) by 1223 days.

This patent is subject to a terminal disclaimer.

(21) Appl. No.: 11/768,874

(22) Filed: Jun. 26, 2007

(65) Prior Publication Data
US 2008/0004539 A1 Jan. 3, 2008

Related U.S. Application Data

(63) Continuation-in-part of application No. 10/378,341, filed on Mar. 3, 2003, now Pat. No. 7,376,457.

(60) Provisional application No. 60/805,864, filed on Jun. 26, 2006, provisional application No. 60/360,930, filed on Mar. 1, 2002.

(51) Int. Cl.
A61B 5/04 (2006.01)

(52) U.S. Cl. ....................................................... 600/515
(58) Field of Classification Search ........... 600/509–519
See application file for complete search history.

(56) References Cited

U.S. PATENT DOCUMENTS

| 5,105,354 | A | | 4/1992 | Nishimura | |
|---|---|---|---|---|---|
| 5,201,321 | A | | 4/1993 | Fulton | |
| 5,291,400 | A | * | 3/1994 | Gilham | 600/509 |
| 5,365,426 | A | | 11/1994 | Siegel et al. | |
| 5,560,370 | A | * | 10/1996 | Verrier et al. | 600/518 |
| 5,682,901 | A | * | 11/1997 | Kamen | 600/519 |
| 6,144,878 | A | | 11/2000 | Schroeppel et al. | |
| 6,212,427 | B1 | | 4/2001 | Hoover | |
| 6,259,944 | B1 | * | 7/2001 | Margulis et al. | 600/509 |
| 6,301,499 | B1 | | 10/2001 | Carlson et al. | |
| 6,330,469 | B1 | | 12/2001 | Griffin et al. | |
| 7,252,637 | B2 | | 8/2007 | Ebner et al. | |
| 2001/0008954 | A1 | * | 7/2001 | Levitan et al. | 600/515 |
| 2002/0169365 | A1 | * | 11/2002 | Nakada et al. | 600/300 |
| 2004/0019289 | A1 | | 1/2004 | Ross | |
| 2005/0143668 | A1 | | 6/2005 | Lu et al. | |
| 2005/0154326 | A1 | | 7/2005 | Martynenko et al. | |
| 2005/0251424 | A1 | * | 11/2005 | Sanders et al. | 705/3 |

OTHER PUBLICATIONS

Sakai, C. et al, "Thought field therapy clinical applications: utilization in an HMO in behavioral medicine and behavioral health services," Journal of Clinical Psychology, Oct. 2001, p. 1215-1227, vol. 57, No. 10, 2001 John Wiley & Sons, Inc.

Niskanen, J. et al, "Software for advanced HRV analysis," Sep. 4, 2002, University of Kuopio-Department of Applied Physics, Report No. 2/2002, p. 1-11, Finland, Internet: URL: http://bsamig.uku.fi/pdf/HRVdeprep.pdf.

(Continued)

Primary Examiner — Carl H Layno
Assistant Examiner — Luther Behringer
(74) Attorney, Agent, or Firm — Kilpatrick Townsend & Stockton LLP

(57) ABSTRACT

Assessing health condition of an animal under study includes receiving heart rate information of the animal under study and performing heart rate variability (HRV) analysis on the received heart rate information for determining autonomic dynamics of the animal under study with respect to a species of which the animal under study is a member, wherein the HRV analysis relates to time domain HRV data and frequency domain HRV data of the received heart rate information that are evaluated with respect to physiological states and corresponding health condition for the time domain HRV data and frequency domain HRV data for the species of the animal under study.

27 Claims, 25 Drawing Sheets

OTHER PUBLICATIONS

Hagen, K. et al, "Heart rate variability in dairy cows—influences of breed and milking system," *Physiology & Behavior*, Jun. 2, 2005, p. 195-204, vol. 85, No. 2, Elsevier Science Ltd., Oxford, GB.

"Heart rate variability: standards of measurement, physiological interpretation, and clinical use," *Circulation*, 1996, p. 1043-1065, vol. 93, No. 5, American Heart Association, Inc., Dallas, TX, USA.

"Heart rhythm scanner, heart rate variability analysis system, user's manual," 1998-2005, p. 1-72, Ver. 2, Biocom Technologies, Internet: URL: http://www.biocomtech.com/HRS%20Manual.pdf.

"Heart rate variability (HRV) as a measure of autonomic regulation of cardiac activity," E. von Borell and TF-3 HRV, Institute of Animal Breeding and Husbandry with Veterinary Clinic, Martin-Luther-University Halle-Wittenberg, Final Meeting of COST Action 846, Bratislava, Mar. 23-24, 2006, Internet: http://www.cost846.unina.it/final_meeting/final_meeting/pdf/Von%20Borell%20COST%20846%20Bratislava%2023-3-2006.pdf.

"Heart rate variability in BSE", Vet. Rec. 139(25):631, Dec. 21-28, 1996, reference only.

"Heart rate variability in Doberman Pinchers with and without echocardiographic evidence of dilated cardiomyopathy", Am. J. Vet. Res. 61(5):506-11, May 2000, abstract only.

Berntson, Gary G. et al., "Heart rate variability: origins, methods, and interpretive caveats", Psychophsiology 34:623-648 (1997).

Bowen, M. et al., "Heart rate variability", Cardiology of the Horse 11:161-76 (1999).

Calvert, C.A., "Heart rate variability", Vet. Clin. North Am. Small Animal Pract. 28(6):1409-27, viii, Nov. 1998, abstract only.

Houle et al., "Low-frequency component of the heart rate variability spectrum: a poor marker of sympathetic activity", Am. J. Phisiol. 276(1Pt2:H215-23), Jan. 1999, abstract only.

International Search Report for PCT Application No. PCT/US03/06431.

Jonker et al., "Characteristics of fetal heart rate changes during the expulsive stage of bovine parturition to fetal outcome", Am. J. Vet. Res. 57(9):1373-81, Sep. 1996.

Kawase et al., "Heart rate variability during massive hemorrhage and progressive hemorrhagic shock in dogs", Can. J. Anaesth 47(8):807-14, Aug. 2000.

Kuwahara et al., "Influence of training on autonomic nervous function in horses: evaluation by power spectral analysis of heart rate variability", Equine Vet. J. Suppl. 30:178-80, Jul. 1999.

Matsunaga et al., "Spectral analysis of circadian rhythms in heart rate variability of dogs", Am. J. Vet. Res. 62(1):37-42, Jan. 2001, abstract only.

Minors et al., "Heart rate variability in the dog: is it too variable?", Can. J. Vet. Res. 61(2):134-44, Apr. 1997, abstract only.

Mohr, E. et al., "Heart rate variability a noninvasive approach to measure stress in calves and calves", Physiology & Behavior 75:251-259 (2002) Elsevier.

Ohmura et al., "Effects of atropine injection on Heart rate variability in thoroughbred horses", J. Vet. Med. Sci. 63(12):1359-1360 (2001).

Physick-Sheard et al., "Frequency domain analysis of heart rate variability in horses at rest and during exercise", Equine Vet. J. 32(3):253-62 (2000).

Pougatchev, V. et al., "Biocom heart rhythm scanner users manual", Heart Rate Variability Analysis Systems Users Manual Version 2.0, www.biocomtech.com 1998-2002.

Thayer et al., "Heart rate variability during exercise in the horse", Biomed. Sci. Instrum. 34:246-51 (1997) abstract only.

Thayer et al., "Heart rate variability in the horse by ambulatory monitoring", Biomed Sci. Instrum. 33:482-5 (1997).

Tygesen et al., "Intensive home-based exercise training in cardiac rehabilitation increases exercise capacity and heart rate variability", Int. J. Cardiol. 79(2-3):175-82, Jul. 2001, abstract only.

\* cited by examiner

ANALYSIS OF HEART RATE VARIABILITY DATA IN ANIMALS FOR HEALTH CONDITIONS ASSESSMENT

CROSS-REFERENCES TO RELATED APPLICATIONS

This application is a continuation-in-part application of co-pending U.S. patent application Ser. No. 10/378,341 to Christine Ross filed Mar. 3, 2003, which claims the benefit of priority under 35 U.S.C. §119(e) of U.S. Provisional Application No. 60/360,930 to Christine Ross filed Mar. 1, 2002. This application also claims the benefit of priority under 35 U.S.C. §119(e) of U.S. Provisional Application No. 60/805,864 filed Jun. 26, 2006 to Christine Ross. The contents of these priority applications is hereby incorporated by reference for all purposes.

BACKGROUND OF THE INVENTION

1. Field of the Invention

The present invention relates generally to health care for animals and, more particularly, to diagnostic testing of animal cardiovascular systems for analysis of animal health.

2. Description of the Related Art

In health care services, the job of the veterinarian in determining animal health is made more difficult because the veterinarian's patient cannot describe symptoms and problems. For even the most common ailments, the veterinarian must rely on keen powers of observation. Many tools, diagnostic and/or prognostic parameters, and modalities have been developed for assessment and evaluation of the health status of an animal.

HRV as an Indicator of Health

One of the animal parameters being studied as an indicator of animal health condition is that of heart rate variability (HRV). In general, HRV refers to the variation in the interval between beats of the heart. For example, HRV data can describe the variation in the R-R interval that occur as a normal physiological response, such as the internal response to neuronal or endocrine influences, or variations in heart rate that occur in response to external stimuli. Some studies have shown that HRV data is a non-invasive indicator of the autonomic nervous system (ANS) activity, and an indicator of the sympathetic and parasympathetic influences upon heart beat rate and rhythm.

HRV is relatively well-studied in human medicine, especially with respect to: the respiratory system and its effect on HRV (known as respiratory sinus arrhythmia); cardiac events; the vasomotor system and baroreceptor variation in heart rate and blood pressure (e.g., Mayer waves); the thermoregulatory system; the renin-angiotensin system and the central nervous system. In veterinary medicine, utilization of heart rate variability data for animal health condition assessment is being studied, but useful results have proven somewhat elusive.

HRV in Animal Studies

Some studies have concluded that HRV analysis can provide useful indicators of animal health, while other studies suggest that contradictory or inconsistent results have been obtained. For example, one study concluded that low frequency (LF) components of HRV indicate sympathetic influences on the heart (Rietmann et al., "The association between heart rate, heart rate variability, endocrine and behavioural pain measures in horses suffering from laminitis" (J Vet Med Animal Physiol Pathol Clin Med 2004 June; 51(5) at 218-25) (data recorded from hospital treatment indicated that LF components of HRV represent mainly sympathetic influences on the heart, whereas high frequency (HF) components of HRV are mediated by the parasympathetic tone), whereas another study concluded that HRV was not a reliable indicator (see Houle & Billman, "Low-frequency component of the heart rate variability spectrum: a poor marker of sympathetic activity", Am J. Physiol. 1999 January: 276 (1Pt2:H215-23)). Thus, proper analysis of HRV data must be carefully performed, with care taken in selecting the proper data parameters to collect and in analyzing the collected data, in order to support valid conclusions about the health of an animal.

It is important that the data collection process itself should be convenient and not overly intrusive to the animal and the owner. Sophisticated laboratory instrumentation systems can collect very precise data streams, but typically they require multiple electrodes and even animal restraints, and the animal being studied may be so upset or hampered by the instrumentation that the collected data is affected and is not reliable. Moreover, the laboratory setting itself is not conducive to collection of valid data from an animal. In addition, unlike humans, most animals are prone to resist cooperating with diagnostic procedures and are not likely to treat equipment with care. To increase the likelihood of collecting valid data, it is important that the data collection mechanism is as minimally intrusive as possible.

Thus, it is important to collect accurate, reliable data of the correct type, to properly analyze the collected data, to draw the right conclusions from the data, and to do so without great inconvenience and without great imposition on the animal and animal owner.

It should be apparent that there is a need for techniques that provide a convenient and non-intrusive means for collecting heart rate data on animals and that collect and analyze proper data parameters and perform appropriate analysis to assess the health and/or condition of an animal under study to assess pain, stress, degree of athletic fitness, fatigue, and systemic compromise. The present invention satisfies this need.

SUMMARY

Assessing health condition of an animal under study includes receiving heart rate information of the animal under study and performing heart rate variability (HRV) analysis on the received heart rate information for determining autonomic dynamics of the animal under study with respect to a species of which the animal under study is a member, wherein the HRV analysis relates to time domain HRV data and frequency domain HRV data of the received heart rate information that are evaluated with respect to physiological states and corresponding health condition for the time domain HRV data and frequency domain HRV data for the species of the animal under study. The heart rate information includes data relating to heart beats, heart rate, and/or interbeat interval (IBI). The health condition report can include analysis and prediction of the health condition of the animal under study, as well as the performance of the animal. In this way, a convenient and non-intrusive means for collecting heart rate and/or IBI data on animals is provided that collects and analyzes proper data parameters and performs appropriate analysis to assess the health condition of an animal under study and to assess pain, stress, degree of athletic fitness, and systemic compromise. The collection and analysis can be performed using techniques that are efficient with respect to system resources, so that collection and analysis can occur in real time. Thus, the convenience and usefulness of the system are enhanced.

In another aspect, the invention provides a method of assessing health condition of an animal under study by receiving heart rate and/or IBI data from the animal under study over a wireless communication link until sufficient data has been collected for reliable health condition assessment of the animal under study, transmitting the received heart rate variability data to a network processor, comparing the received heart rate variability data at the network processor against corresponding heart rate variability data for known healthy condition animal, determining health condition of the animal under study in response to the comparison, generating a health condition report for the animal under study based on the determined autonomic dynamics, determining standard deviation data for variation between heart beats of the received heart rate variability data, determining total power, determining high frequency (HF) and low frequency (LF) components of the received heart rate variability data, determining a plot of the HF and LF components and identifying quadrants of the plot that correspond to predetermined health condition states. The plot can include a ln-ln plot of ln(LF) and ln(HF) data, and the health condition report can indicate and/or predict an unhealthy or unfavorable condition of the animal under study if at least one data point of the log-log plot exceeds a predetermined value.

Other features and advantages of the present invention will be apparent from the following description of the embodiments, which illustrate, by way of example, the principles of the invention.

DETAILED DESCRIPTION

Figure 1:
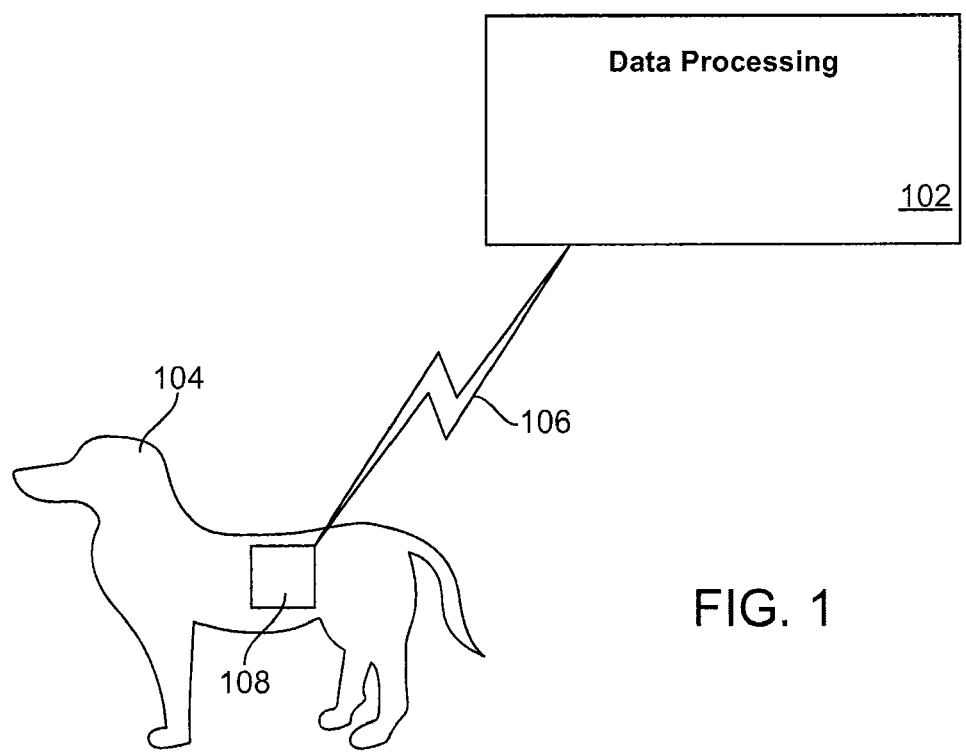
FIG. 1 is a representation of a heart rate variability processing system constructed in accordance with the present invention.

FIG. 1 shows a heart rate variability processing system constructed in accordance with the present invention. A data processing apparatus 102 of the system receives heart rate information from an animal under study 104 over a non-invasive data link 106. The heart rate information may include heart rate data, heart beat data, interbeat interval (IBI) data, total power, low frequency (LF) components of IBI data, high frequency (HF) components of IBI data, and the like. The data processing apparatus 102 receives the heart rate and/or IBI data, generates heart rate variability data, performs data analysis on the heart rate variability data, and determines health condition of the animal under study. The animal 104 can comprise any variety of non-human animal, such as a dog, cat, horse, livestock, exotic, aquatic, marine animal, and the like, for which heart rate and/or IBI data can be collected. The data processing apparatus 102 can comprise a hand-held computing device that receives the heart rate information and then passes the information to a data processing subsystem of the apparatus, or the apparatus 102 can comprise a single, integrated device that performs all the functions of data collection, data analysis, and data reporting. In either case, it is not necessary to attach bulky equipment and cumbersome electrode patches and wires to the animal. Rather, data collection is a non-invasive experience for the animal and is easy for an operator to perform, and generates report data that can be used to determine animal health and/or condition. It is important that the animal under study should remain at rest, so as to stabilize the animal's condition and provide reliable and accurate heart beat information. Under some situations, it might be necessary to exercise minimal restraint, such as tethering or caging, so as to ensure that the animal remains at rest during data collection.

The data analysis involves determining autonomic dynamics of the animal under study 104, followed by determining health condition of the animal under study based on the determined autonomic dynamics, and generating a corresponding health condition report for the animal. In this way, the apparatus 102 provides a convenient and non-intrusive means for obtaining heart rate data on animals and collects and analyzes proper data parameters and performs appropriate analysis to assess the health and/or systemic (overall) condition of an animal under study to assess pain, stress, degree of athletic fitness, fatigue, and systemic compromise.

The data processing apparatus 102 can receive the heart rate information directly from the animal 104, or the apparatus can receive the information from a wireless heart data sensor apparatus 108 that transmits the information from the animal to the apparatus. For example, acoustic, visual, thermal, or electromagnetic (e.g. infrared) techniques may be used to receive data directly from the cardiovascular system of the animal 104 by means of emissions or observable phenomenon that emanate 106 directly from the animal, and thereby derive the heart rate information. If the apparatus 102 receives the heart rate information directly, then the apparatus can send a signal to the animal and receive a return signal (e.g. a reflected signal that is modulated by the animal's heart beat) or the apparatus can include passive detection by means of receivers to detect acoustic, visual, thermal, or electromagnetic (e.g. infrared) energy emanating from the animal and incorporating heart beat information. Alternatively, the apparatus 102 may receive the heart rate information from the sensor apparatus 108, which may include one or more heart information transducers and communications interfaces that detect the heart rate information and transmit the data from the transducers to the data processing apparatus 102 over a wireless data link 106. The sensors 108 can be strapped to the animal in a non-restrictive fashion, so as not to cause the animal undue stress or otherwise hinder accurate and reliable data collection. Alternatively, the animal sensors 108 can comprise one or more wireless transmitters that are implanted or ingested prior to the time of data collection, so that no further intrusion to the animal is necessary.

The data processing apparatus 102 can provide an assessment of the health condition of the animal under study 104 after receiving the heart rate information from the animal until sufficient data has been collected for reliable health condition assessment, performing heart rate variability analysis on the received heart rate and/or IBI data for determining autonomic dynamics of the animal under study, and generating a health condition report for the animal under study based on the determined autonomic dynamics. The apparatus thereby provides a convenient and non-intrusive means for collecting heart rate and/or IBI data on animals that collects and analyzes proper data parameters and performs appropriate analysis to assess the health condition of an animal under study and to thereby assess pain, stress, degree of athletic fitness, fatigue, systemic compromise, and aspects of emotion (e.g., anxiety).

Figure 2:
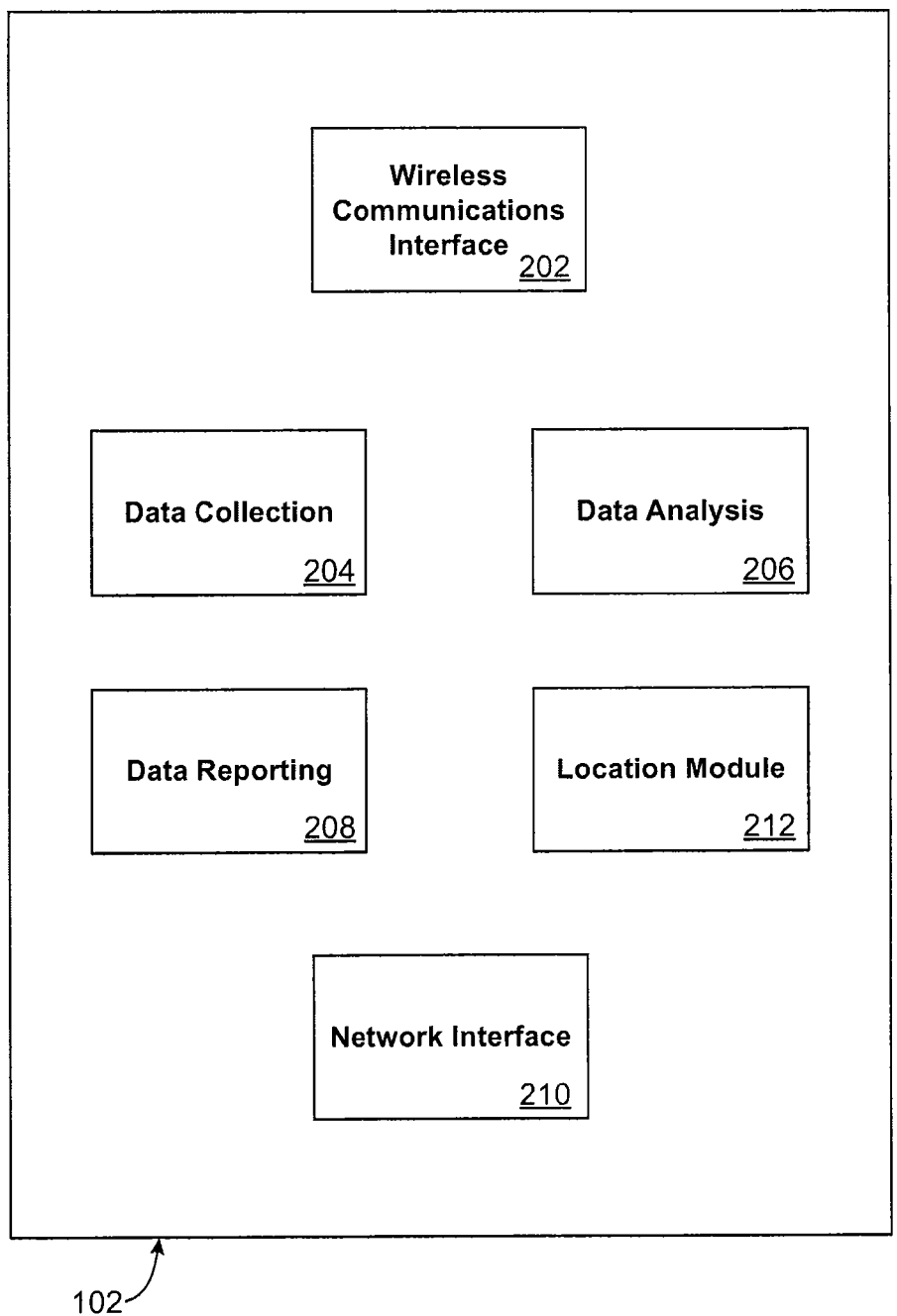
FIG. 2 is a block diagram of the data processing unit illustrated in FIG. 1.

FIG. 2 is a block diagram of the data processing apparatus 102 illustrated in FIG. 1 and shows that the apparatus includes a wireless communication interface 202, a data collection unit 204, a data analysis unit 206, a data reporting unit 208, and a network interface 210. A location module 212 can be included, such as a Global Positioning System (GPS) receiver unit that can accurately determine the geographical position of the data collection operation (and thereby determine the geographical position of the animal under study). These components 202-212 can be incorporated into a single device with an integrated display, such as a notebook computer or handheld computer, a personal digital assistant (PDA), or smart phone, or these components can comprise multiple independent devices, each of which performs one or more of the functions illustrated in FIG. 2.

The wireless communication interface 202 enables communication between the data processing apparatus 102 and the wireless heart rate sensor 108 (FIG. 1). The data collection unit 204 receives data from the wireless communication interface 202 and stores it for processing by the data analysis unit 206. The data may be stored in a temporary buffer of the data collection unit 204 for being streamed to the data analysis unit 206 or may be sent to an external data store. If the data processing apparatus 102 receives heart beat information directly from the animal, then the data collection unit 204 may incorporate transmitting and/or receiving equipment for receiving the information from the animal. Examples of receiving information directly from the animal can include detection of heart beat information from thermal or infrared indicators (such as eardrum measurements) or optical indicators (such as eye (pupil) indicators) or acoustic or other information emitted by the animal, including quantum teleportation and entangled photon phenomena as a means of such data communication to the apparatus.

The data analysis unit 206 has sufficient computational resources to perform heart rate variability analysis on the collected data. The data reporting unit 208 incorporates an input/output facility so that commands can be received by a system user and so that the health condition of the animal under study can be received by a system user. The network interface 210 is an optional component that can comprise an interface to a network by wireless or wired (cable) means, such as connection to the Internet or to a local area network. The network interface also can comprise an interface for connection with an external device, such as for wireless communication with an external data store, printer, data port, or server, by means of the Bluetooth data standard or the like.

Some of the components 202-212 can be deleted if not necessary. For example, if the apparatus 102 receives heart beat information directly from the animal, then it might be unnecessary to include a wireless communication interface 202 with the apparatus. In that circumstance, the wireless communication interface would be replaced by a suitable direct information interface, such as the infrared, thermal, optical, acoustic, and quantum teleportation schemes described above.

Figure 3:
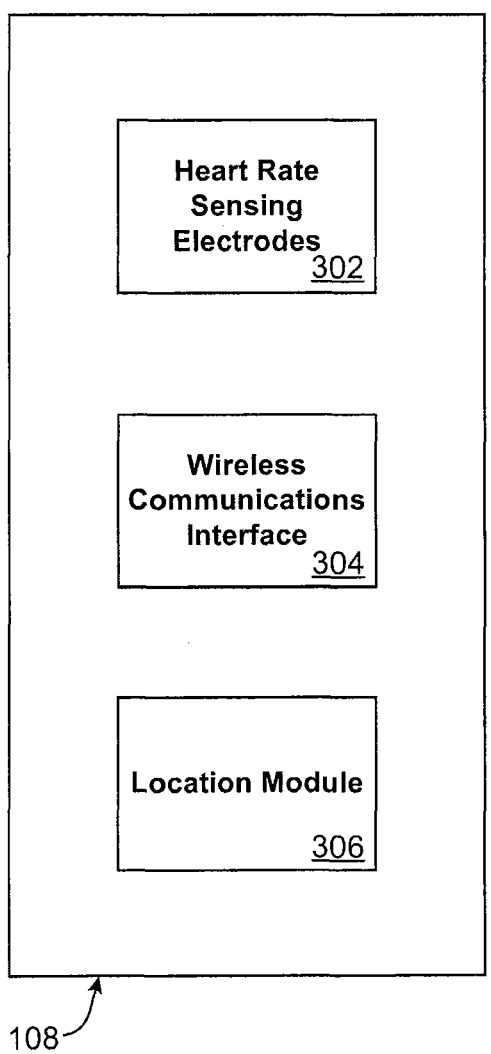
FIG. 3 is a block diagram of the wireless heart rate sensor illustrated in FIG. 1.

FIG. 3 is a block diagram of the wireless heart rate sensor 108 illustrated in FIG. 1, and shows that the sensor includes heart rate sensing electrodes 302, such as are well known in the art, and a wireless communications interface 304 that permits communication between the sensing electrodes and the data processing apparatus 102 (via the wireless communication interface 202 of the data processing unit). The electrodes 302 are capable of recording heart rate and/or IBI data in millisecond (msec) intervals, to ensure that the electrodes can capture data at sufficient rates to provide high frequency (HF) and low frequency (LF) components of the heart rate variability data. In particular, the electrodes 302 capture heart rate and/or IBI data at 1 msec intervals. The communication interface 304 can incorporate a data logger that captures the sensor data and for collection and transport. FIG. 3 shows that the sensor package 108 can optionally include a location module 306, such as a GPS receiver unit that can accurately determine the geographical position of the sensor 108 (and thereby determine the geographical position of the animal under study). The GPS capability enables monitoring location of animals, such as wild, endangered, or exotic species, and enable determining extent of habitat, migration and health of a group or herd or flock, and also to locate sentinel animals under study, such as for monitoring environmental conditions or concerns for pollution. Other purposes can be facilitated with the GPS location monitoring capability, such as crustacean monitoring for bioterrorism events or joint monitoring of location and heart beat information for animals under study to detect alert responses (such as stress, anxiety, and the like) in conjunction with environmental monitoring and surveillance efforts and the like. The GPS capability is also useful for companion animals and pets, to automatically monitor the location and health condition of such animals when an owner or caretaker is away. As described further below, alert messages can be automatically generated upon the occurrence of predetermined health conditions of the animal and/or location of the animal.

Figure 4:
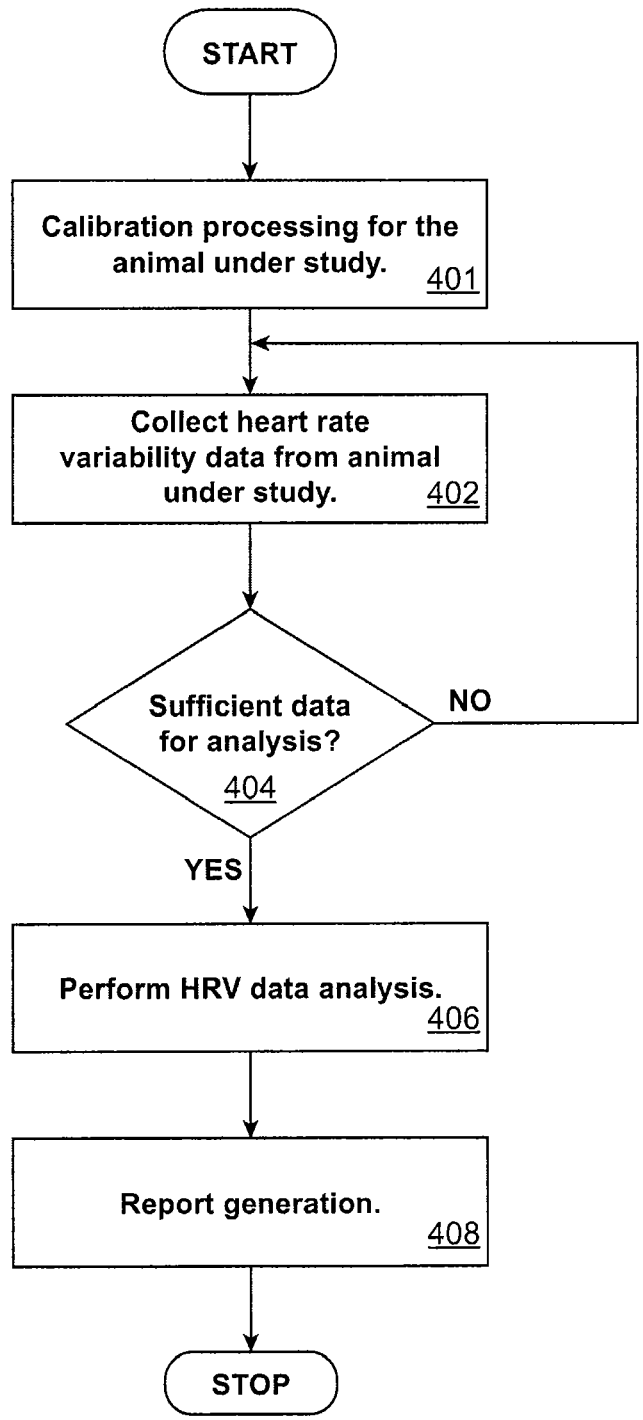
FIG. 4 is a flow diagram of the processing carried out by the system illustrated in FIG. 1.

FIG. 4 is a flow diagram of the processing carried out by the system illustrated in FIG. 1. In the first operation, represented by the flow diagram box numbered 401 in FIG. 4, the system performs a calibration processing operation for the animal under study. In normal processing, this is an optional, preliminary step, because prior data typically would have been previously collected for the particular animal under study when in a healthy condition. Alternatively, the data collected in the calibration processing operation 401 may comprise at-rest data for one or more healthy animals similar to the animal under study. That is, if at-rest data in a healthy condition is not available for the actual animal under study, then collected data for one or more similar animals in good health will suffice for operation of the system. Thus, the calibration data comprises data sufficient to establish a baseline of heart rate variability data for one or more animals similar to the animal under study who are in a known healthy condition. The collected calibration data can be retrieved from a data store of the system, or from a network data store. In normal operation of the system, the user will be queried as to whether calibration data for the animal under study is being collected, or if heart rate and/or IBI data is being collected for the animal under study for the purpose of diagnostic operations. Thus, the system user will have control over whether the first illustrated operation 401 will be performed or if it is not necessary.

The next operation in FIG. 4, indicated by the box numbered 402, represents the first operation of normal diagnostic processing, in which the data processing apparatus 102 (FIG. 1) collects heart rate and/or IBI data from the animal 104 and produces heart rate variability data. The data is typically collected in sufficiently small data intervals of 1 msec, so that all phases of the cyclic heart rhythm are obtained, to include high frequency components (HF) as well as low frequency components (LF). Those skilled in the art will understand that different animals under study may require different data collection frequencies or intervals, depending on normal at-rest heart beat rates for the animal under study and other individual animal and species differences. Moreover, other data frequency components may be utilized. For example, very low frequency (VLF) and ultra low frequency (ULF) HRV data can be utilized for animals under study. Those skilled in the art will know that ULF for humans is less than approximately 0.003 and VLF in man=0.003–0.040, whereas for horses VLF=0.001–0.005 (from Bowen and Marr).

At the next operation, represented by the decision box 404, the data processing unit checks to determine if sufficient data has been collected to ensure reliable diagnostic conclusions. For a typical domesticated animal, such as a horse, dog, or cat, data should be collected for approximately five minutes. This amount of time increases the chance that any anomalies in the animal's heart rhythm will not overwhelm the collected data and skew the diagnostic results. Those skilled in the art will understand that it is likely the amount of time for minimal data collection will be different for different species of animals under test and for different circumstances and equipment.

If a sufficient amount of time has elapsed (that is, if sufficient heart rate and/or IBI data has been collected from the animal under study), an affirmative outcome at the decision box 404, then processing continues at the next operation 406. If a sufficient amount of heart rate and/or IBI data has not been collected, a negative outcome at the decision box 404, then processing returns to the data collection operation 402.

After sufficient data has been collected at 404, then at the next operation 406 the processing apparatus performs heart rate variability (HRV) data analysis. In accordance with the invention, the HRV data analysis includes (but is not limited to) determining autonomic dynamics of the animal under study, determining standard deviation data for variation between heart beats of the received heart rate variability data (SDNN), determining Total Power, determining high frequency (HF) and low frequency (LF) components of the received heart rate variability data, and determining a plot of the HF and LF components and identifying quadrants of the plot that correspond to predetermined health condition states. The plot can comprise, for example, a plot of ln(LF) against ln(HF) for the IBI heart rate variability data. The predetermined health condition states can comprise, for example, states of stress, pain, general health, and peak performance.

It is important that the collected data should be reliable and accurate. As noted above, care should be taken to ensure that the conditions under which the data collection occurs will provide reliable data. Therefore, the data analysis operation at 406 can include a data review and edit operation. The data review and edit operation provides an opportunity to check the collected data for anomalies or other indicators of unreliability. For example, it might be apparent that the animal under study was not at rest during the time of data collection, in that the data shows wide variations across the entire data collection session. It might be apparent that singular events (such as a brief animal movement or startle event) might result in isolated unreliable data points. In those conditions, the system can permit deletion of particular data points or sessions that are anomalies or otherwise unreliable. Such data review and edit can be performed manually, by giving the user of the data collection device the opportunity to review and edit the data. Alternatively, the system itself can be configured to check the collected data for indicators of unreliability and issue a warning or alert that the collected data might be suspect, or the system can be configured to delete and/or ignore suspect data, as desired. The data review and edit operation can take into account species differences and animal differences due to circadian rhythms, age, gender, and the like. If review and edit are completed or bypassed, then the data analysis 406 is completed.

After the HRV data analysis has been performed at 406, the system next generates a health condition report, as indicated at box 408. The health condition report is based on the HRV data for the animal under study and, more particularly, is based on the determined autonomic dynamics of the animal. Those skilled in the art will appreciate that "autonomic dynamics" refers to data representing a ratio of parameters relating to the sympathetic and parasympathetic systems. The ratio is typically expressed as a ratio of HF to LF components of HRV data. Other components of the health condition report can include, for example, data relating to the standard deviation of intervals between heart beats (referred to as SDNN) and total power generated by the animal under study. Other data parameters may include, for example, a plot on a log scale (ln) for LF components of HRV on the horizontal (x) axis and for HF components of HRV on the vertical (y) axis. That is, ln(LF) appears on the x-axis and ln(HF) appears on the y-axis. Additional parameters may be included, as desired.

In one embodiment, the HRV data analysis involves time domain HRV parameters (such as HF and LF data) and frequency domain parameters (such as total power and HF and LF data), and the HRV data analysis also involves evaluation of the time domain and frequency domain parameters with respect to physiological states and corresponding health condition data for the species of the animal under study.

For example, the physiological states and health condition data can include the numerical values for time domain HRV parameters and numerical values and ranges for frequency domain HRV parameters for each species to be considered (i.e., subject to test and report). As a point of comparison, exemplary values of humans for HRV data include the following range: LF=0.04–0.15; HF=0.15–0.40 (man), and corresponding values for horses would be the following range: LF=0.01–0.07; HF=0.07–0.06 (horse). Such information for animals to be considered can be contained in suitable databases for use by the system. Also included in a suitable database would be information relating to the normal physiological states for the species under consideration, e.g., vagal (parasympathetic) tone predominates in the horse to give a slow resting heart rate (normal for a horse, however a resting heart rate of 40 is not normal for a human). Heart rate is a time domain HRV parameter. Additional information to be known for the HRV analysis includes environmental information and corresponding normal behavior for the species in that environment. That is, it is important to know the normal behavior of the animal species within certain environments, because an animal's physiology (and therefore it's HRV data) is dependent upon, and affected by, its environment and the demands that are being put on the animal, e.g., performance, production, breeding, and the like. See, for example, "Heart Rate Variability" by M. Bowen, Chapter 11 in *Cardiology of the Horse*, C. Marr (ed.), W B Saunders (1999) at p. 163 ("The use of HRV analysis in the horse has been questioned due to the horse's labile response to environmental stimuli. Although the effect of environment, both physical and emotional, has not been fully established in human beings, environmental modification is essential to ensure reproducible data in the horse.").

For purposes of a clinical HRV tool such as described herein, it is important to identify environmental conditions with certain HRV parameters in order to have a clinically valuable (i.e., reproducible) tool. For example, excessively high HRV values when a horse is first placed on a transport van is a normal physiological occurrence. Such values are indicative of a horse under stress and experiencing anxiety. Thus, the HRV parameters, their numerical values, ranges, and relationship to each other, are considered and evaluated to identify and/or quantify a specific animal clinical condition, such as "pain" for the breed/species under consideration, within a particular environment, performing a specific task or in the particular state of existence. See, for example, the data represented in Table 1 below, comprising the type of data contained in a suitable database in connection with the present invention. It should be understood that a condition table such as the data in Table 1 cannot be used for animals other than the animal breed/species for which it was intended (in the case of Table 1, intended for the horse). That is, data sets corresponding to the information in Table 1 are necessary for each of the animals/species/breeds under consideration. It may be noted that there will likely be more species differences than there will be differences across breeds.

The data processing apparatus 102 (FIG. 1) includes sufficient computing and communicating resources that the data collection, data analysis, and data reporting can occur substantially in real time. Thus, a data collection session that lasts approximately five minutes can conclude with a substantially contemporaneous report of the animal's health and condition. For example, the health condition report can generally be produced in sufficiently quick succession after the data collection that a deleterious health condition can be determined and appropriate action can be taken.

Figure 5:
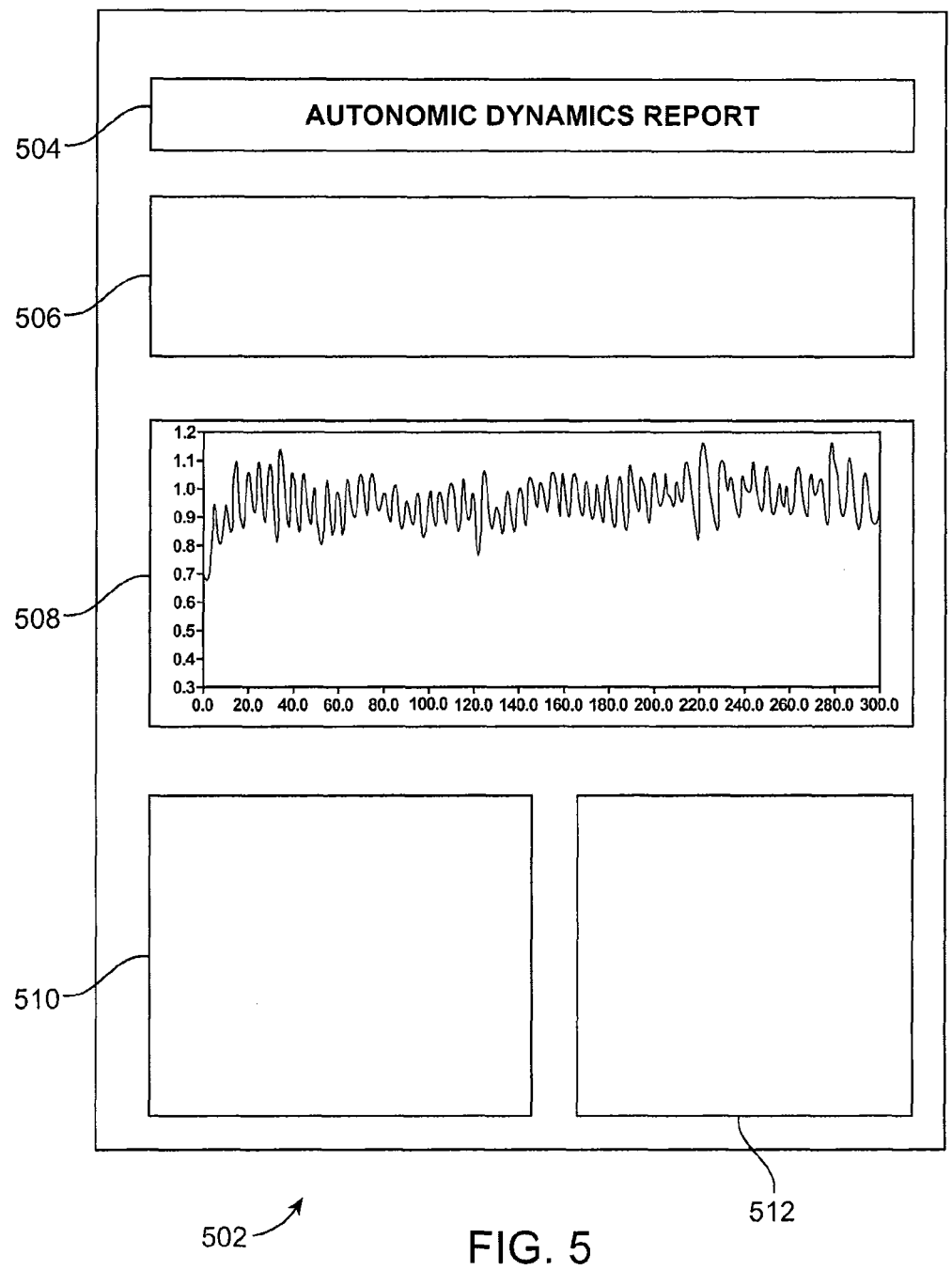
FIG. 5 is an illustration of a health condition report produced by the system illustrated in FIG. 1.

FIG. 5 is an illustration of a health condition report 502 produced by the system illustrated in FIG. 1. The health condition report 502 can be produced on a display of the data processing unit 108 (FIG. 1) or can be produced in graphical output format, such as a document that can be printed. If desired, the health condition report can include a health signal, such as a warning light or approval light that can be illuminated if the corresponding health condition is determined. The output shown in FIG. 5 is given the title "Autonomic Dynamics Report" to emphasize that the health condition report is based on autonomic dynamics i.e., a summation of influences acting upon, and generated by, the central nervous system (CNS) as they modulate the relative influence and function of the sympathetic and parasympathetic branches of the autonomic nervous system (ANS) of the animal under study, as represented by the autonomic dynamics graph described below. The next block 506 of the report 502 includes data in a tabular format, such as a data table, so that quantitative output can be reviewed by the user. A graphical representation of the heart rate and/or IBI data (tachogram) occupies the next output block 508, which is illustrated in FIG. 5 as a plot of interbeat interval (IBI) data.

If desired, the data block 508 can include multiple graphical representations of heartbeat data, such as including both electrocardiogram data and tachogram data. Graphical representation of data such as in block 508 is often easier to grasp for health care professionals and can often provide for quicker evaluation of data. Moreover, the ECG wave can be used for recognition of interbeat intervals via R-wave detection, in accordance with processing for species differences in physiology. For example, there are many conditions in horses that can cause very big T-waves (e.g., performance horses who are sweating and experiencing electrolyte changes). The analysis processing of the system can be configured to recognize the largest wave as the R-wave (QRS deflections), and when serum potassium changes occur, for example, the processing will start identifying the T-waves and the R-waves when the T-waves get as tall as R-waves, rendering the data useless (alternatively, the collected data could be edited to remove all the T-waves). Therefore, R-wave recognition in horses may be better accomplished by looking at the velocity or speed of the wave deflection rather than the amplitude, because the deflection of R-waves (ventricular depolarization) will be more rapid than the relative deflection of T-waves (ventricular repolarization). Thus, ECG analysis may be more useful under some conditions than tachogram analysis. In either case, the system analysis can be performed on the tabular data underlying the graphs or on the graphical data. The illustrated report 502 includes both tabular (numerical) 506 data presentation and graphical data 508 presentation.

An autonomic dynamics graph 510 occupies the next block of the health condition report 502. As described in greater detail below, the autonomic dynamics graph is a graphical plot on a log-log scale (ln-ln) for LF components of HRV on the horizontal (x) axis and for HF components of HRV on the vertical (y) axis. That is, ln(LF) appears on the x-axis and ln(HF) appears on the y-axis. Additional quantitative data as desired can be tabulated and shown in the remaining block 512 of the report, and the block 512 can include a health condition conclusion or assessment score. The data of the report 502 may be arranged in configurations other than that shown in FIG. 5.

The autonomic dynamics graph 510 can be configured in a variety of arrangements, and those skilled in the art will understand how to process the HRV data so as to provide the ln(HF) vs. ln(LF) plot. For example, a suitable system for processing such data and producing a suitable autonomic dynamics graph can be provided by the "Heart Rhythm Scanner" product available from Biocom Technologies Inc. of Poulsbo, Wash., USA. Other HRV data processing solutions are available; see, for example, the University of Kuopio, Finland (described at the URL of bsamig.uku.fi/pdf/HRVdeprep.pdf) and J&J Engineering (information available at the Web site of www.jjengineering.com).

The illustrations in FIGS. 6-23 provide examples of autonomic dynamics graphs and tabular data for horses in a variety of conditions. The data was collected from actual data recording sessions from horses in a clinical setting and illustrate the conclusions that can be quickly and reliably reached from analysis of the HRV data, as described above. Thus, the system can collect the HRV data, perform analysis sufficient to determine the autonomic dynamics graph, and make conclusions about the health and condition of the animal under study based on the collected HRV data, all in real time. As described further below, the health condition assessments derived from the information in FIGS. 6-23 involves analysis of the HRV data, such as with respect to the spread of data points on the charts.

Figure 6:
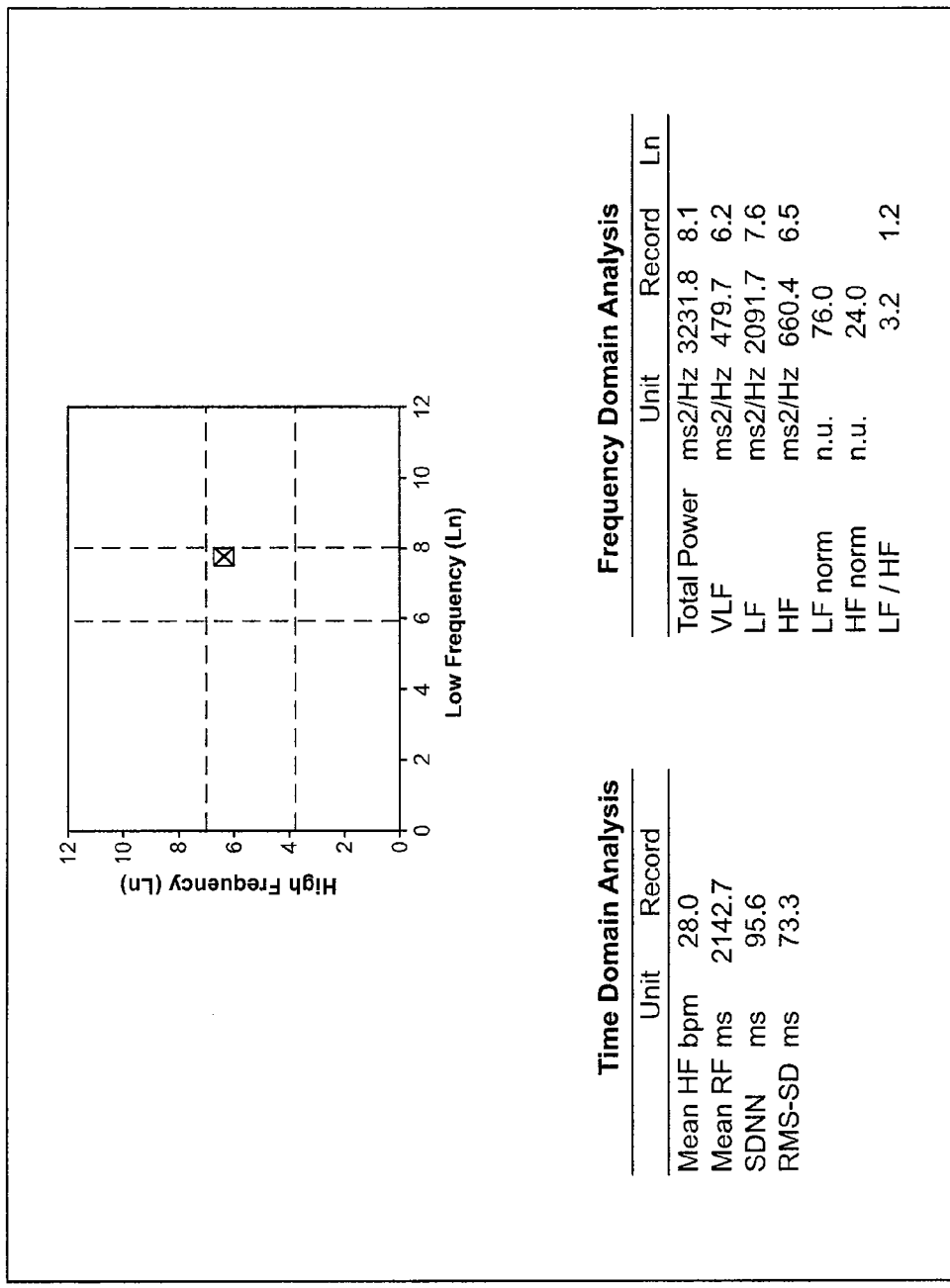
FIG. 6 is an illustration of the autonomic dynamic diagram portion of the report illustrated in FIG. 5 for an animal under study.

FIG. 6 is an illustration of the autonomic dynamic diagram portion 602 of a condition report such as the report illustrated in FIG. 5 for an animal under study. FIG. 6 shows data for a horse that had experienced a tooth extraction at the time of the data gathering. The horse was sedated. The plot of ln(HF), ln(LF) data is indicated by a square in the graph, to show the concentration of data points from the data collection. It should be understood that multiple data points were recorded. Per the description above, the heart beat information from which the FIG. 6 plot was produced comprised approximately five minutes of heart beat information data collected from the horse in 1 msec intervals. The plot of LF, HF data shows that the collected data from this horse lies in the region below about ln(HF)=7.0 along the y-axis and to the left of ln(LF)=8.0 along the x-axis. An animal in this region of the ln(LF), ln(HF) graph is said to be experiencing a pain condition. It should be noted that the data points from the data collection can often be dispersed across the graph area during the data collection time, although the data points will typically concentrate in an elliptical shape tilted toward the upper right corner of the graph, at approximately a 45-degree angle. In fact, the inventor has observed that the data points are often most concentrated in animals having poor health condition, having low data variability and low SDNN.

Figure 7:
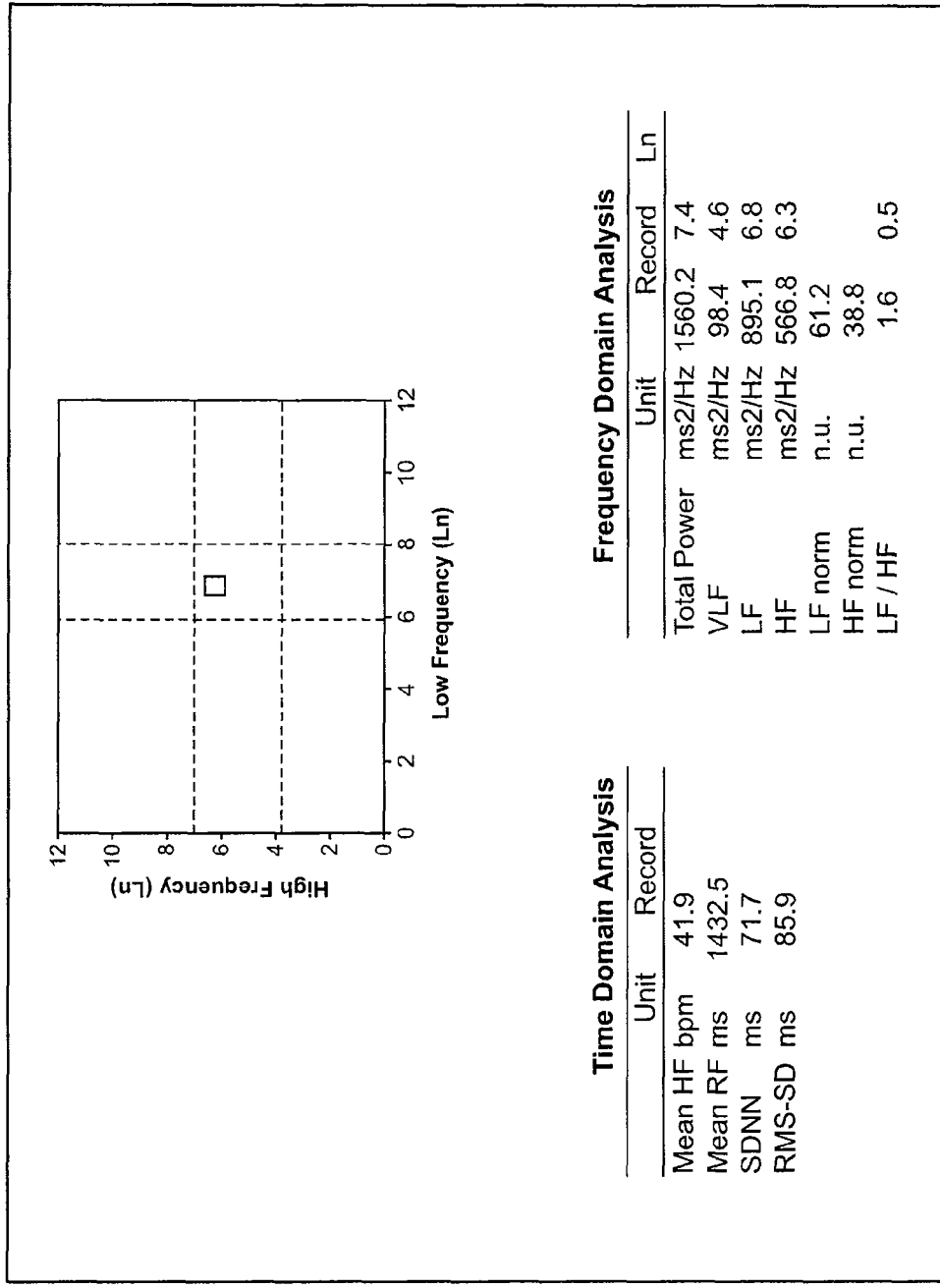
FIG. 7 is an illustration of the autonomic dynamic diagram portion of the report illustrated in FIG. 5 for another animal under study.

FIG. 7 is an illustration of the autonomic dynamic diagram portion 702 of a condition report such as the report illustrated in FIG. 5 for an animal under study. FIG. 7 shows data for a horse suffering from laminitis. Again, the LF/HF data shows data below ln(HF)=7.0 and less than ln(LF)=8.0, showing this horse to be in a pain condition. The reduced total power output may be an indication of sedation. Though the inventor has observed that many horses that are suffering from injury or illness provide a Total Power of less than about 4000 ms2/Hz, the TP may be influenced by sedation or other medication.

Figure 8:
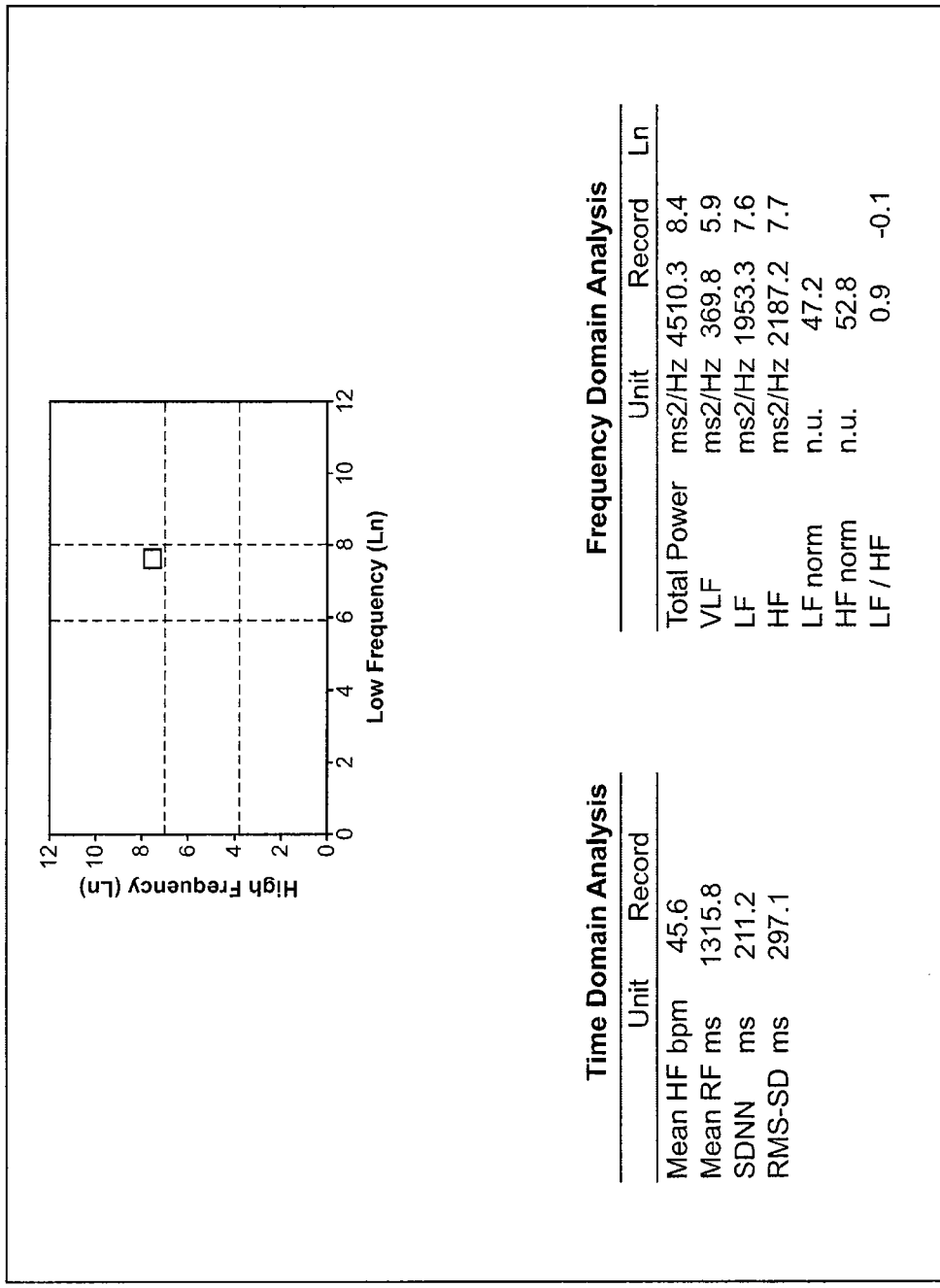
FIG. 8 is an illustration of the autonomic dynamic diagram portion of the report illustrated in FIG. 5 for another animal under study.

FIG. 8 is an illustration of the autonomic dynamic diagram portion 802 of a condition report such as the report illustrated in FIG. 5 for an animal under study. The horse from which the FIG. 8 data was collected had a foot abscess. FIG. 8 shows the horse to have data above ln(HF)=7.0 and ln(LF)=8.0, again indicating a pain condition.

Figure 9:
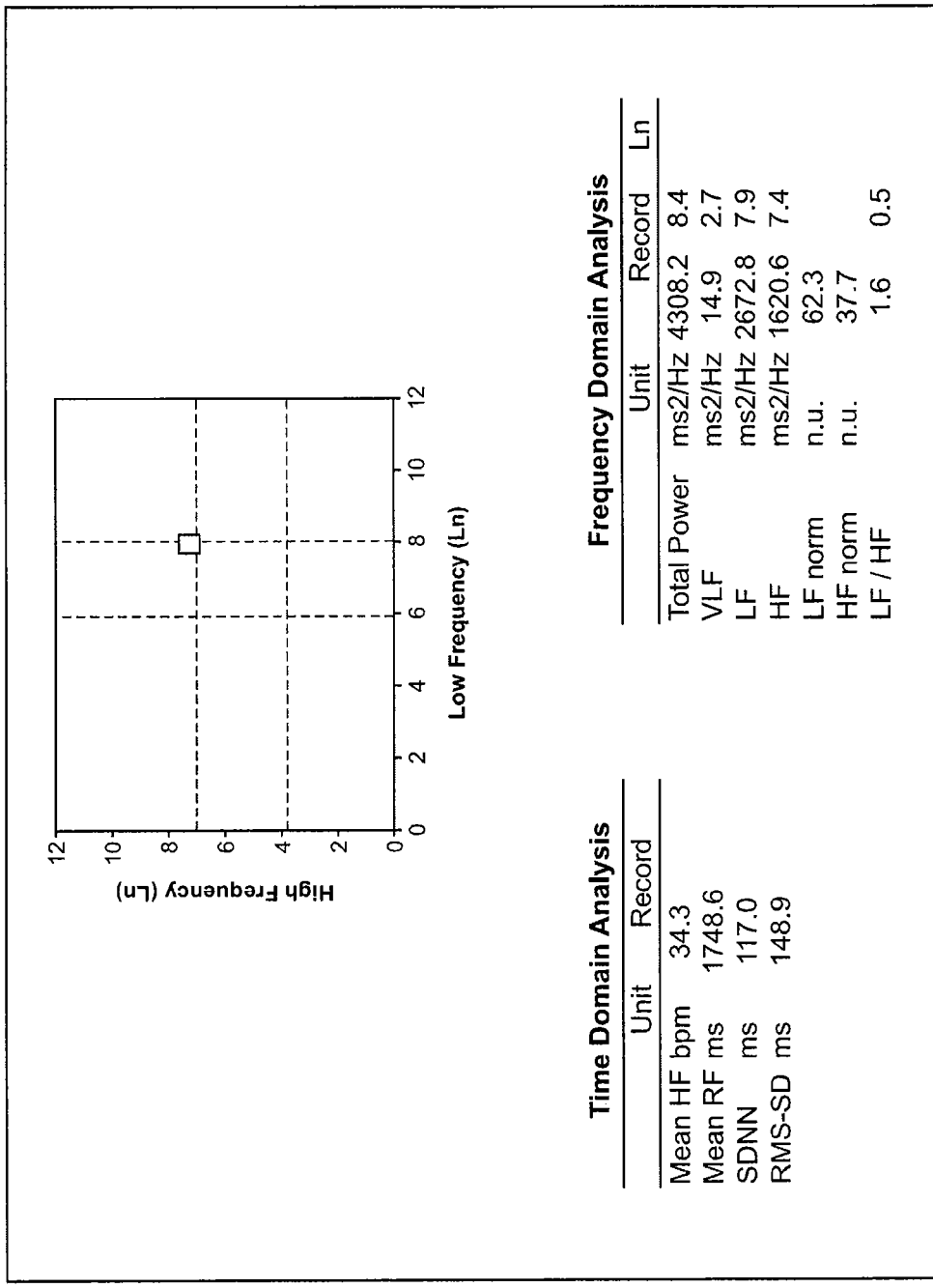
FIG. 9 is an illustration of the autonomic dynamic diagram portion of the report illustrated in FIG. 5 for another animal under study.

FIG. 9 is an illustration of the autonomic dynamic diagram portion 902 of a condition report such as the report illustrated in FIG. 5 for an animal under study. FIG. 9 shows a horse that was experiencing a large submandibular abscess and is similar to the data for FIG. 8, indicating a pain condition.

Figure 10:
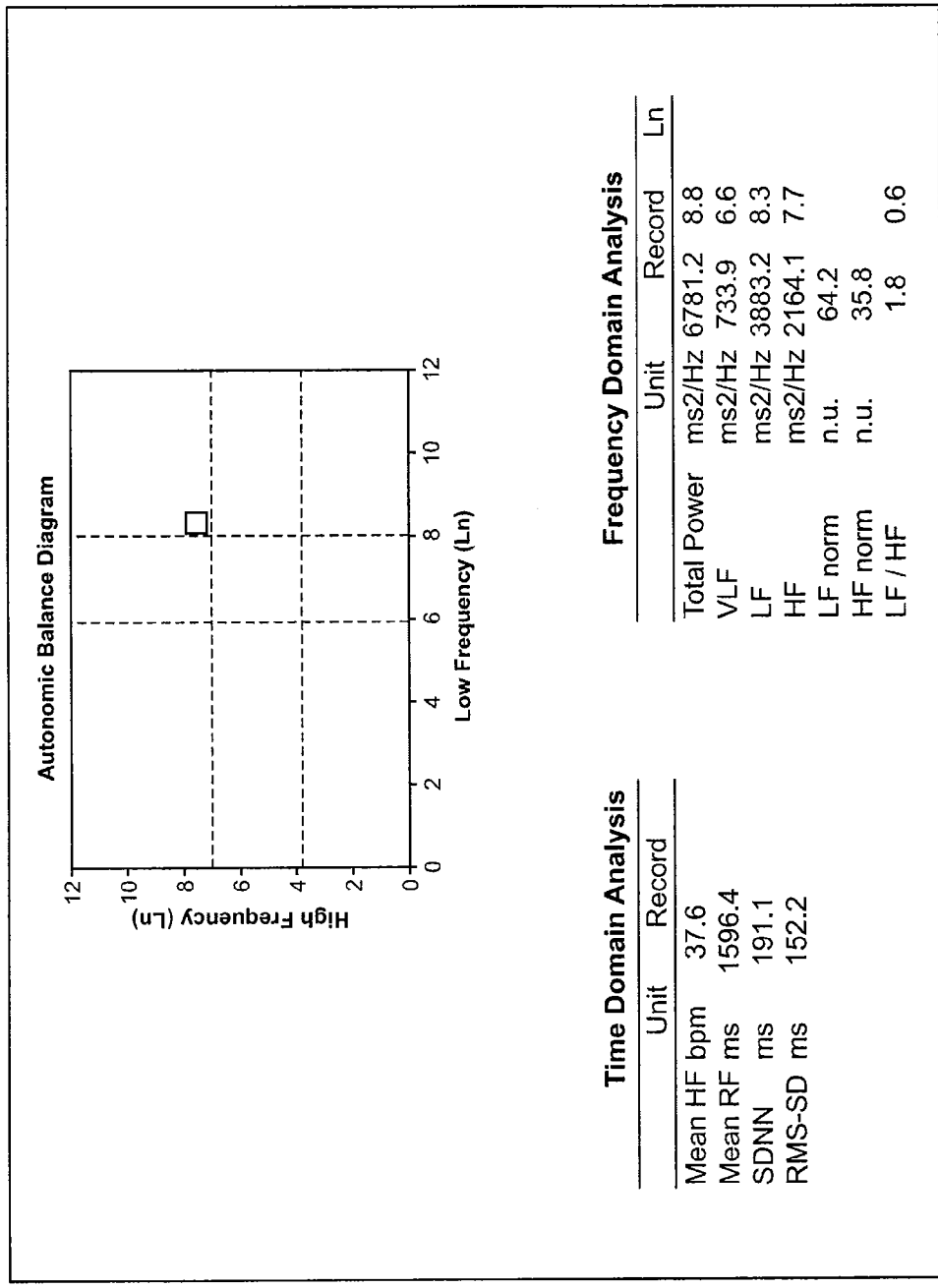
FIG. 10 is an illustration of the autonomic dynamic diagram portion of the report illustrated in FIG. 5 for another animal under study.

FIG. 10 is an illustration of the autonomic dynamic diagram portion 1002 of a condition report such as the report illustrated in FIG. 5 for an animal under study. FIG. 10 shows data from a horse during an examination for purchase and lameness was observable at a trot in all circumstances, i.e., Grade III, AAEP (American Association of Equine Practitioners) Grading System. This horse would be classified as being in a pain condition and a stress condition.

Figure 11:
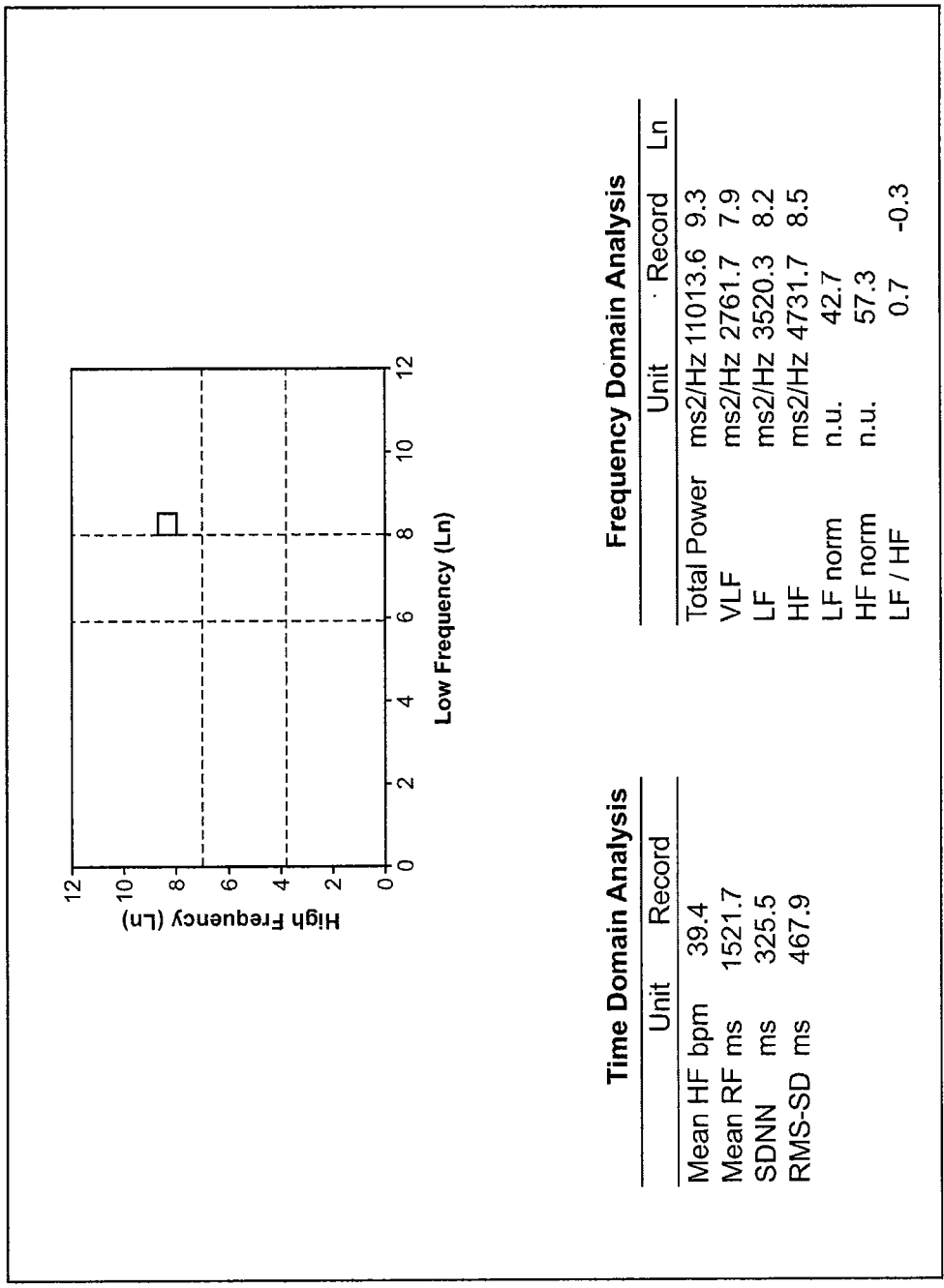
FIG. 11 is an illustration of the autonomic dynamic diagram portion of the report illustrated in FIG. 5 for another animal under study.

FIG. 11 is an illustration of the autonomic dynamic diagram portion 1102 of a condition report such as the report illustrated in FIG. 5 for an animal under study. FIG. 11 shows data from a horse during an examination for purchase and lameness was obvious with marked head nodding, Grade IV, (AAEP Grading System), and would be classified as being in a pain condition and stress condition.

Figure 12:
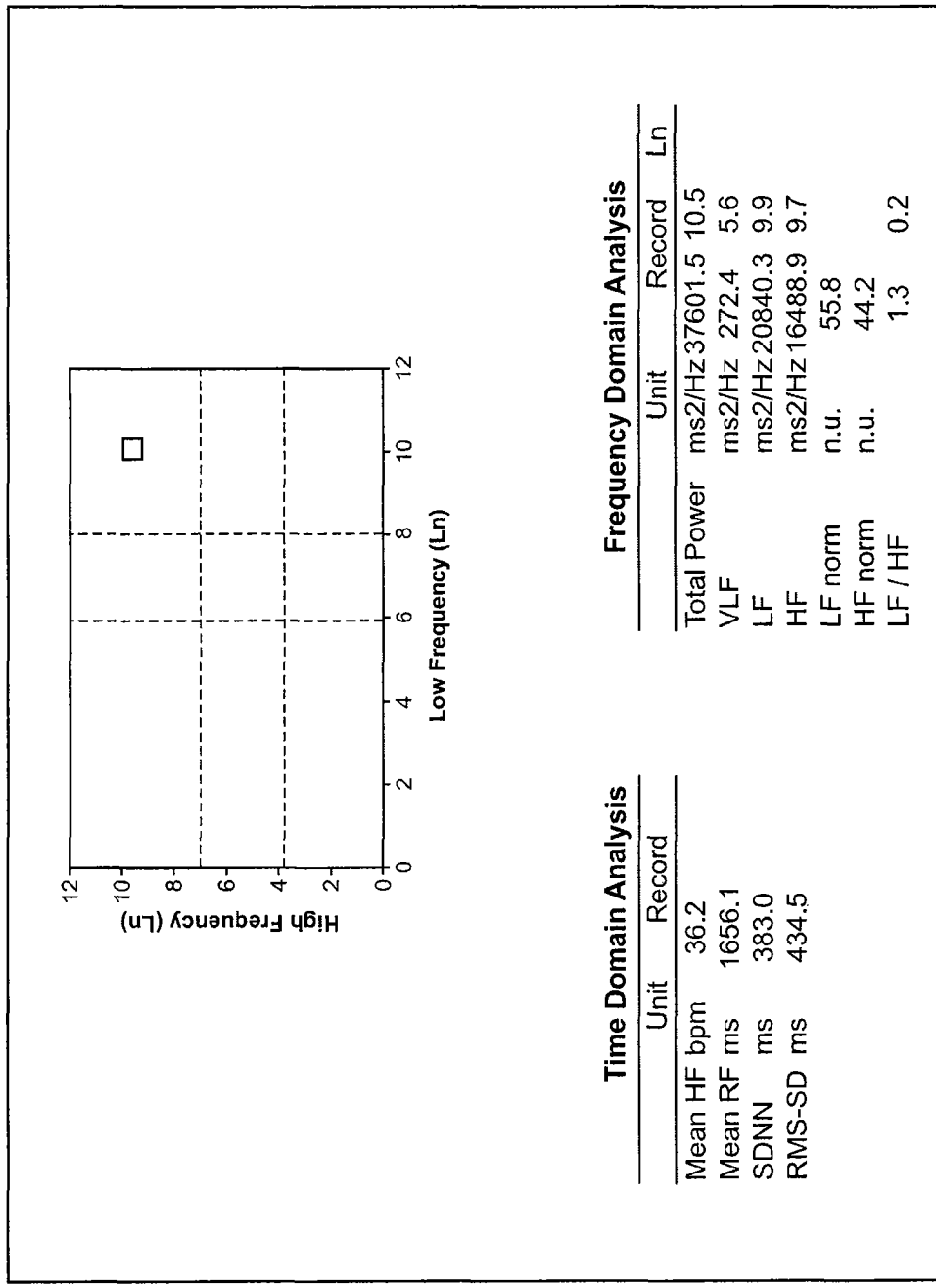
FIG. 12 is an illustration of the autonomic dynamic diagram portion of the report illustrated in FIG. 5 for another animal under study.

FIG. 12 is an illustration of the autonomic dynamic diagram portion 1202 of a condition report such as the report illustrated in FIG. 5 for an animal under study. FIG. 12 shows data from a horse suffering with gastric ulcers (EGUS, Equine gastric Ulcer Syndrome). With the indicated ln(LF)/ln(HF) plot in FIG. 12, this animal would be classified in a stress condition.

Figure 13:
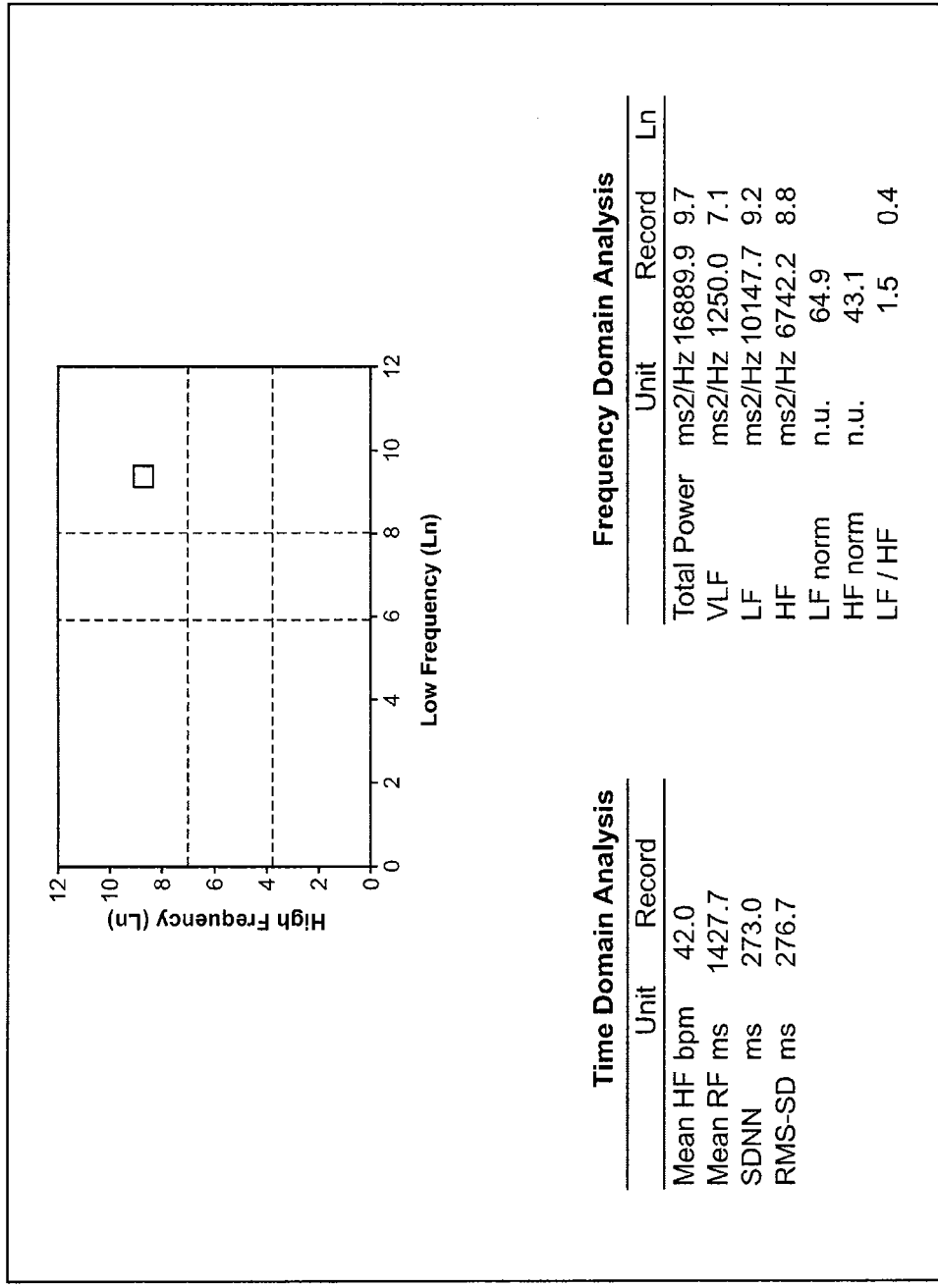
FIG. 13 is an illustration of the autonomic dynamic diagram portion of the report illustrated in FIG. 5 for another animal under study.

FIG. 13 is an illustration of the autonomic dynamic diagram portion 1302 of a condition report such as the report illustrated in FIG. 5 for another animal under study. This horse exhibited nervous behavior (i.e., anxiety) and diarrhea, and would also be classified in a stress condition.

Figure 14:
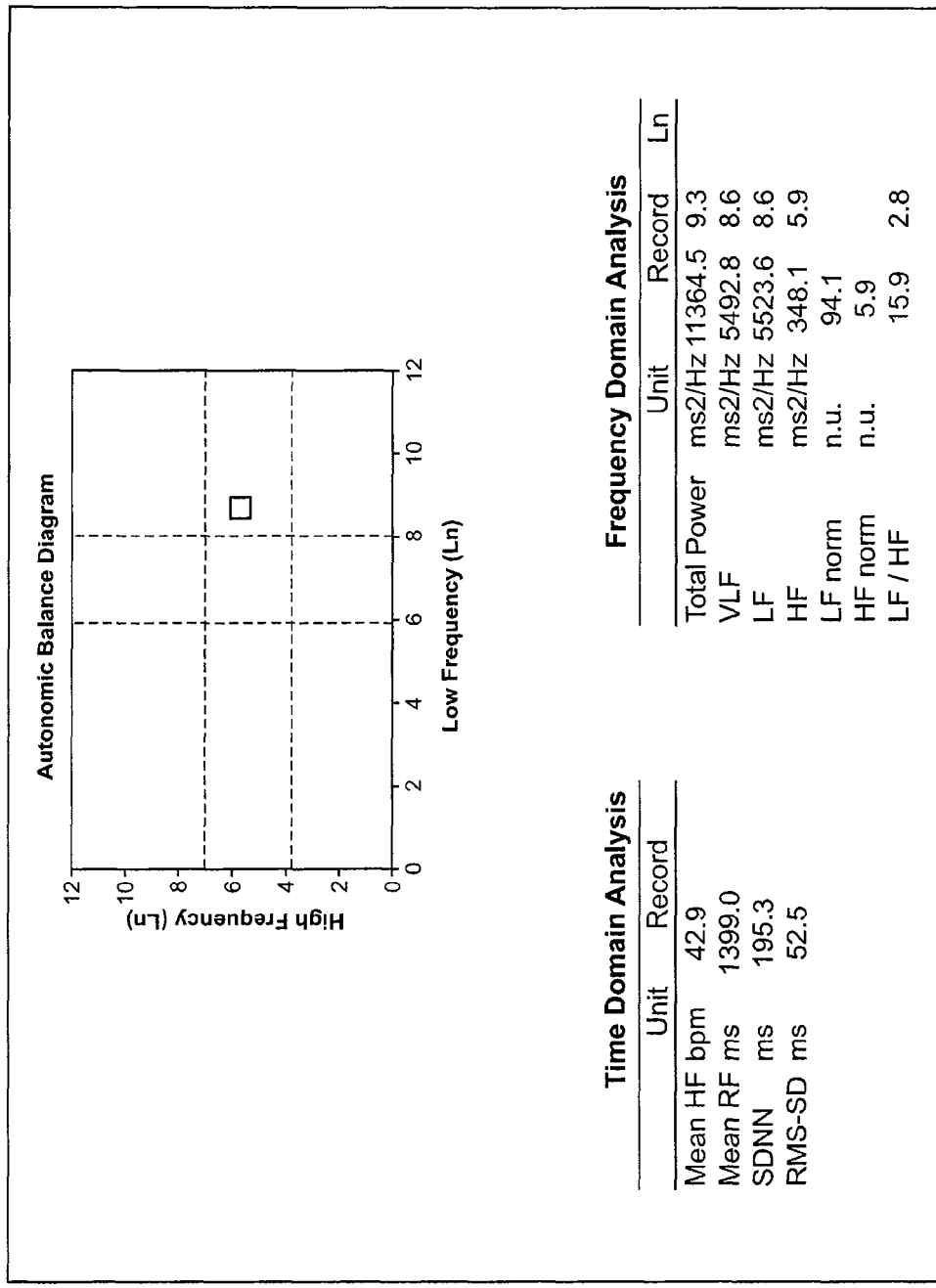
FIG. 14 is an illustration of the autonomic dynamic diagram portion of the report illustrated in FIG. 5 for another animal under study.

FIG. 14 is an illustration of the autonomic dynamic diagram portion 1402 of a condition report such as the report illustrated in FIG. 5 for another animal under study. This horse was a racehorse and was reported as training well (good performance). The data indicates above ln(LF)=8.0 along the x-axis and above ln(HF)=4.0 along the y-axis, with a relatively high power output (11364.5). This horse would be classified in a fit condition, ready to race.

Figure 15:
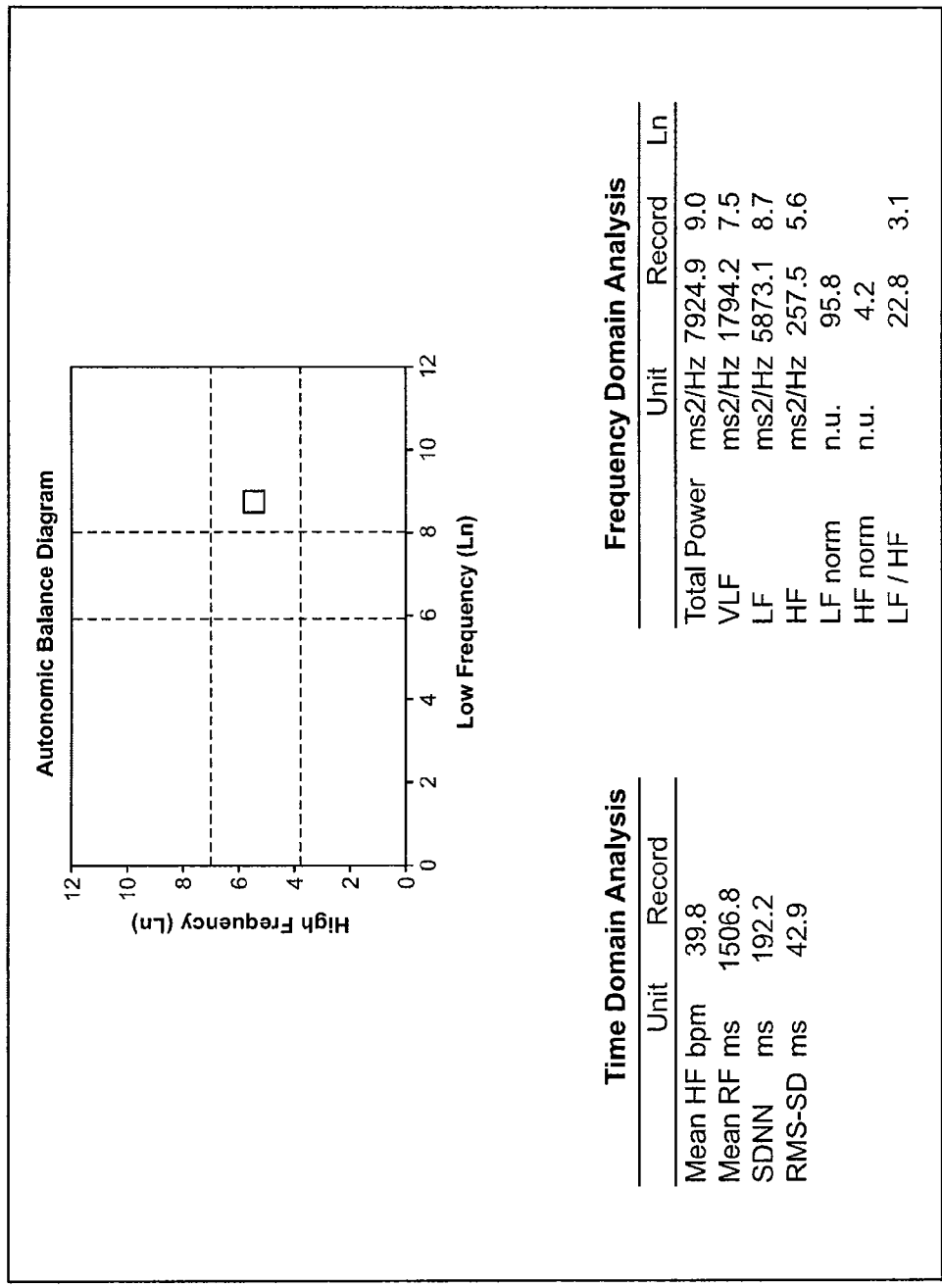
FIG. 15 is an illustration of the autonomic dynamic diagram portion of the report illustrated in FIG. 5 for another animal under study.

FIG. 15 is an illustration of the autonomic dynamic diagram portion 1502 of a condition report such as the report illustrated in FIG. 5 for another animal under study. This horse shows similar data to that of FIG. 14, and also would be classified in a fit condition.

Figure 16:
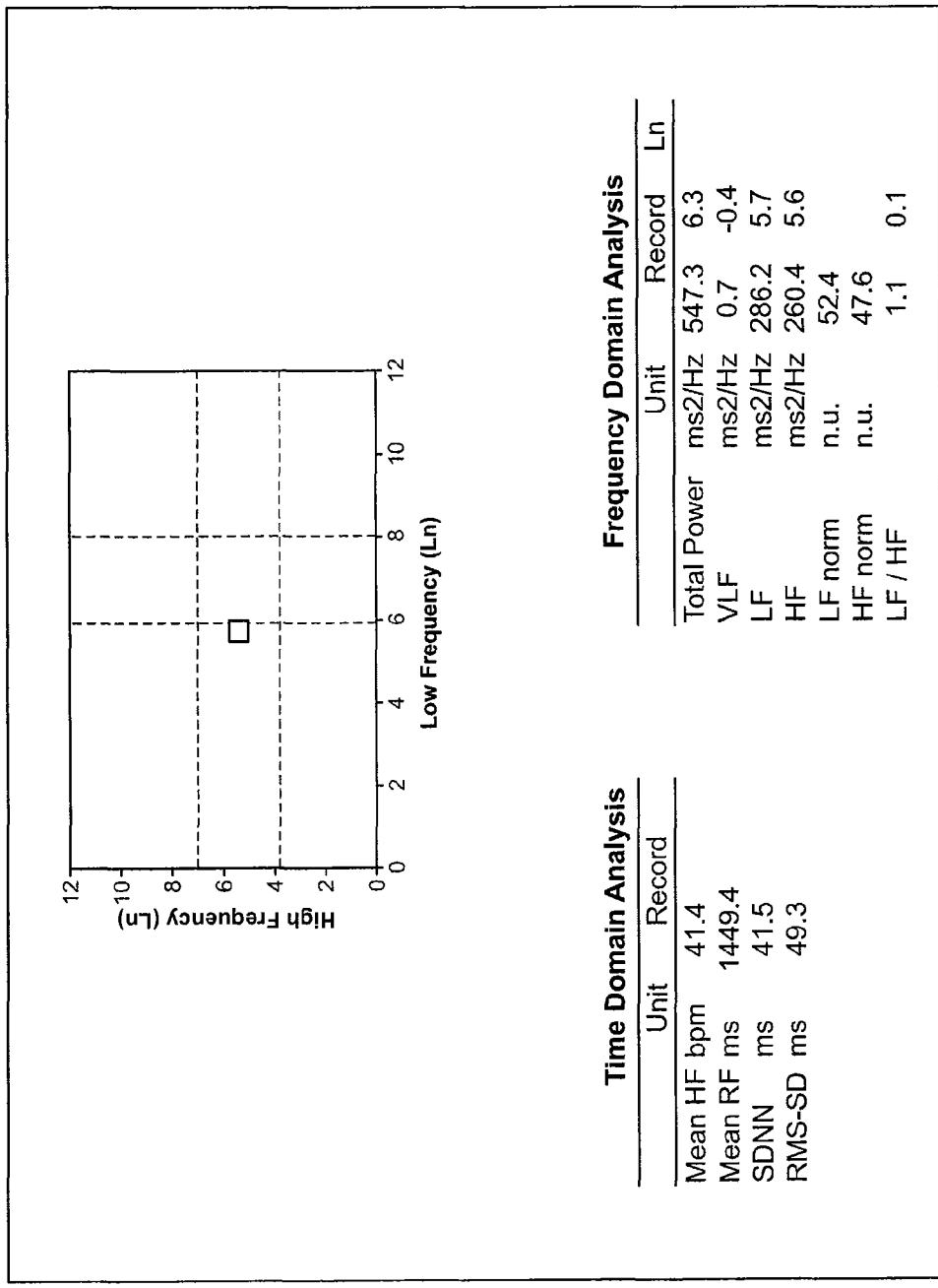
FIG. 16 is an illustration of the autonomic dynamic diagram portion of the report illustrated in FIG. 5 for another animal under study.

FIG. 16 is an illustration of the autonomic dynamic diagram portion 1602 of a condition report such as the report illustrated in FIG. 5 for another animal under study. This horse was a racehorse suffering from pleuropneumonia. The data is below ln(LF)=6.0 along the x-axis and below ln(HF)=6.0 along the y-axis, with a low SDNN value (41.5), and a low Total Power (547.3), and would classify this horse in a systemic compromise condition.

Figure 17:
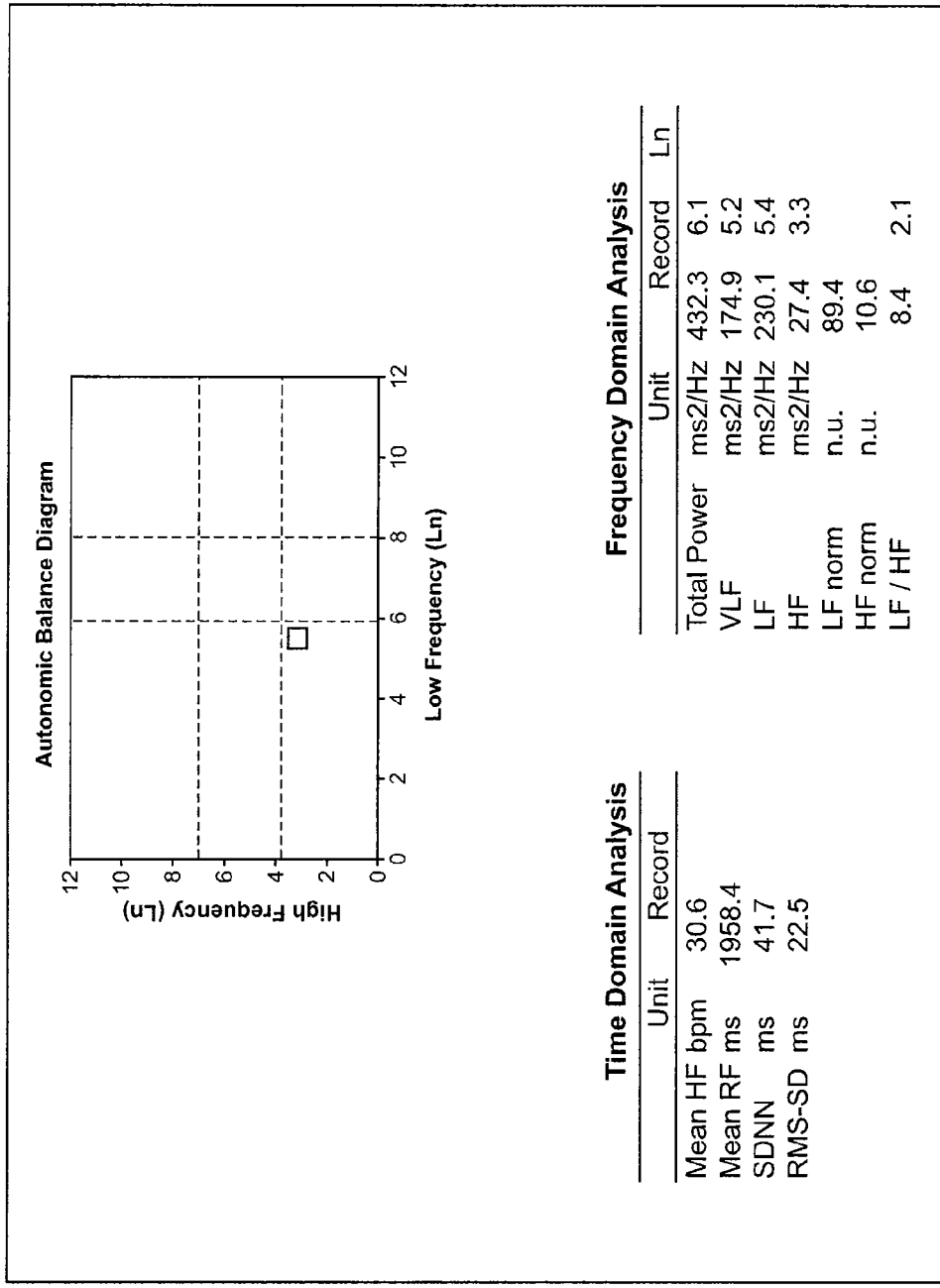
FIG. 17 is an illustration of the autonomic dynamic diagram portion of the report illustrated in FIG. 5 for another animal under study.

FIG. 17 is an illustration of the autonomic dynamic diagram portion 1702 of a condition report such as the report illustrated in FIG. 5 for another animal under study. The data is below ln(LF)=6.0 along the x-axis and below ln(HF)=6.0 along the y-axis. The horse was still in training and recently had an episode of exercise induced pulmonary hemorrhage (EIPH) The horse shows a low SDNN (41.7) and a low Total Power (432.3). The data would classify this horse in a systemic compromise condition.

In the exemplary data charts illustrated herein, a single assessment category (e.g., from among those listed in Table 1) was determined according to a count of data points in corresponding graph areas, such as shown in FIGS. 18-22. That is, in the graphical charts shown in FIGS. 6-17, a small block of the graph was singled out for a health condition assessment and characterization as "pain" or "stress" or "fit" and so forth, but it should be understood that such assessments involve analysis of the data points, such as counting the data points within the corresponding areas of the graphs and determining which graph areas (e.g. pain or stress or fit) contain the greatest number of data points and assigning the health condition assessment to the corresponding characterization. It should be understood that the HRV analysis and health condition assessment could also be determined by mathematical and statistical models for data characterization, as will be known to those skilled in the art.

Figure 18:
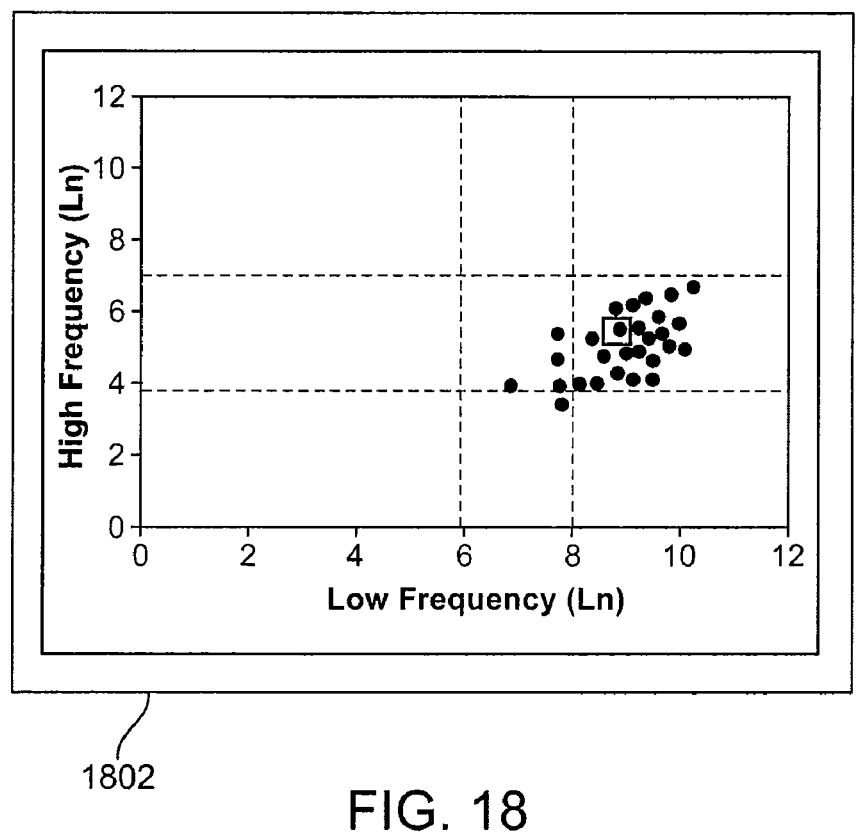
FIG. 18 is an illustration of the autonomic dynamic diagram portion of the report illustrated in FIG. 5 for another animal under study.

FIG. 18 is an illustration of the autonomic dynamic diagram portion 1802 of a condition report such as the report illustrated in FIG. 5 for another animal under study. FIG. 18 shows data points for the plot of ln(LF) and ln(HF), to indicate the spread that may be obtained with actual data collection. The circumstances of data collection should be adjusted as needed to account for species differences, circadian rhythms, and the like to ensure reliable and accurate data. For example, data collection can occur once daily, at approximately the same time every day under similar conditions, over a sequence of consecutive days. In the case of FIG. 18, data points were plotted as twenty-two data points within the "fit" classification (greater than ln(LF)=8.0 and below ln(HF)=7.0), while only five data points were in another classification. Those skilled in the art will understand that the dispersion of points in the illustration is normal for a racehorse in training. Each data point is the result of a single five-minute data collection session, collected on different days. The horse from which the FIG. 18 data was collected won a race during the time of the data collection efforts. The horses from which the data in the other illustrations was collected generally performed well if the data report indicated fitness, or experienced subsequent injury or reduced levels of performance if the data report indicated pain, stress, fatigue, or an otherwise diminished (i.e., not fit) health condition (stress may also be referred to as an "anxiety" state).

Thus, the data identified herein as indicating animal health and condition can be used as a general predictor of performance or fitness, and as a predictor of potential injury. In this way, HRV data collected in a non-intrusive manner in accordance with the invention described herein may be used to determine when an animal, such as a race horse, would not likely perform at an optimal level and would benefit from therapy, such as rest or reduced workload, and can assist with more accurate diagnoses of the animal's health condition. The animal health condition indication techniques disclosed herein can be useful as a risk stratification tool, to use the HRV data analysis in conjunction with HRV parameters to identify animals (such as horses) who might be at risk of injury, catastrophic breakdown, or illness. That is, the techniques described herein, such as illustrated in FIGS. 6-23 and in the accompanying description, can be useful as a predictive tool for animal performance, utilization, and care.

Figure 19:
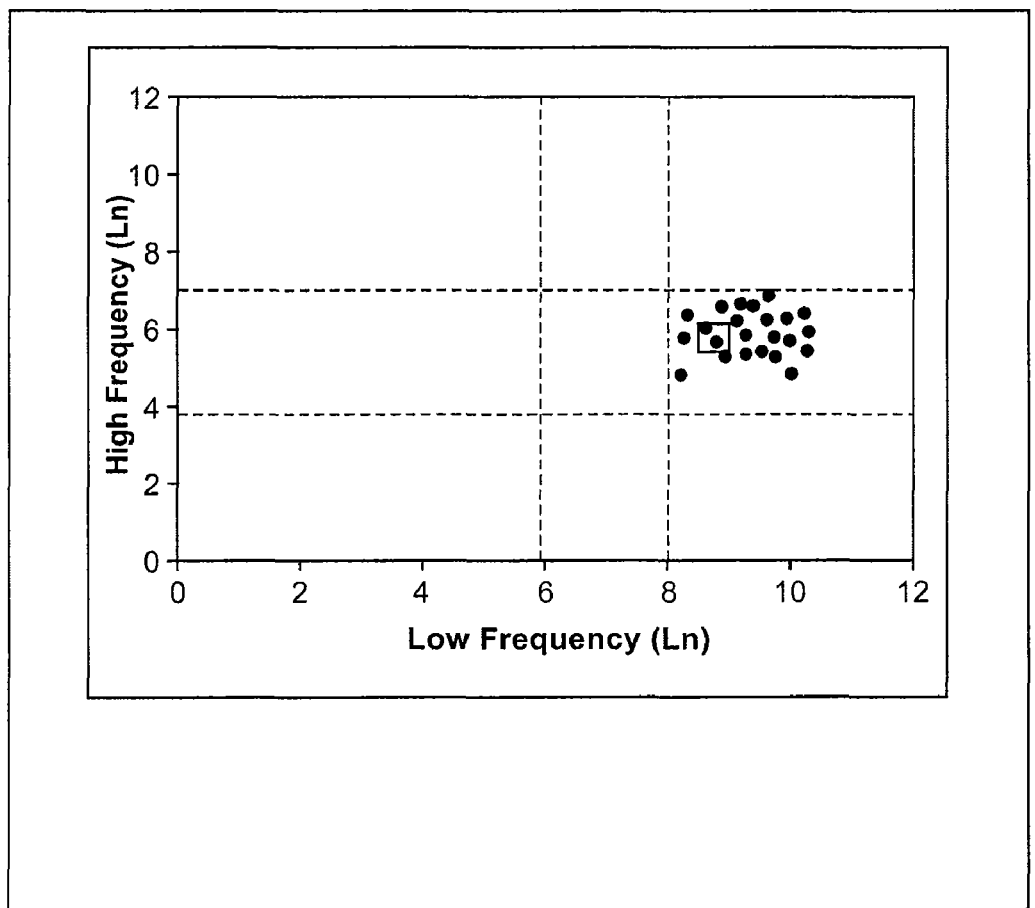
FIG. 19 is an illustration of the autonomic dynamic diagram portion of the report illustrated in FIG. 5 for another animal under study.

FIG. 19 is an illustration of the autonomic dynamic diagram portion 1902 of a condition report such as the report illustrated in FIG. 5 for another animal under study. The horse from which the FIG. 19 data was collected, a racehorse, shows no data points outside of the "fit" condition and twenty-one data points within it. This horse was winning races at the time of the study and following the time of the study.

Figure 20:
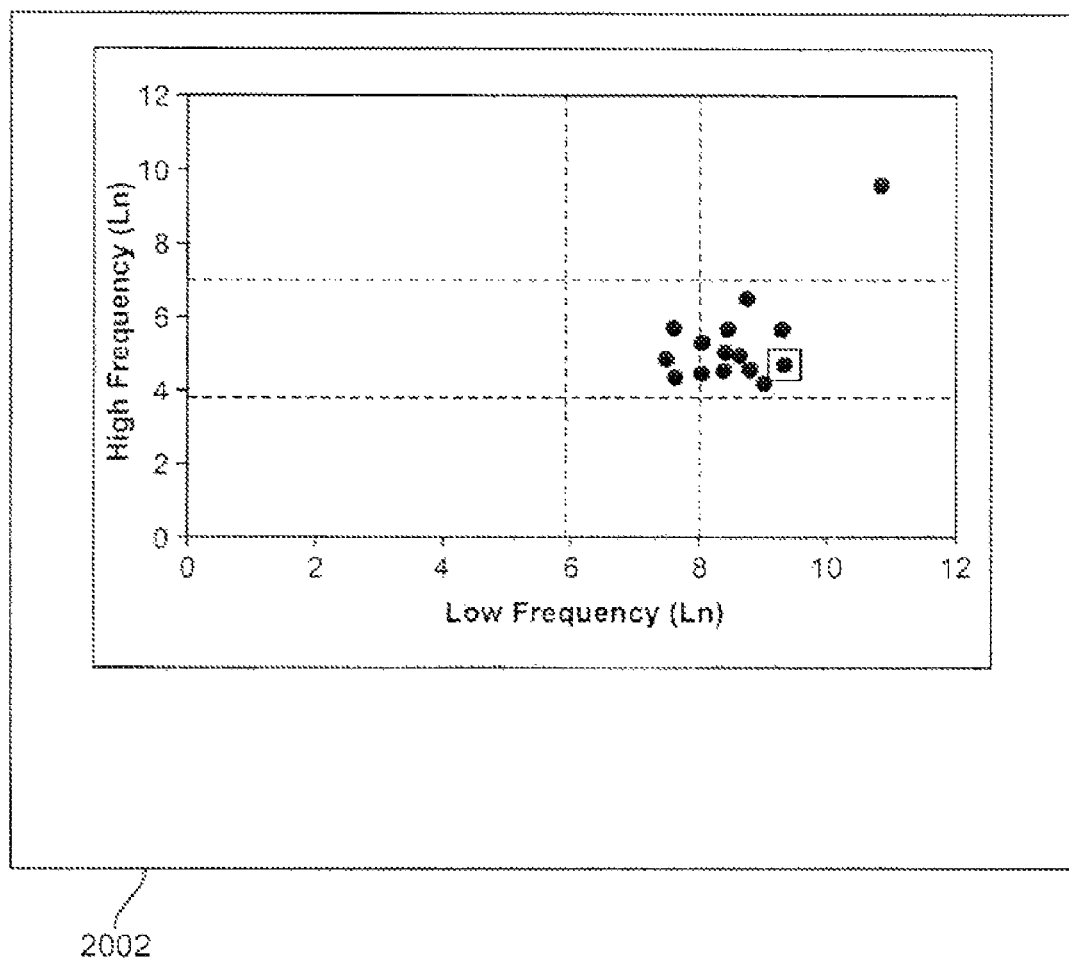
FIG. 20 is an illustration of the autonomic dynamic diagram portion of the report illustrated in FIG. 5 for another animal under study.

FIG. 20 is an illustration of the autonomic dynamic diagram portion 2002 of a condition report such as the report illustrated in FIG. 5 for another animal under study. The horse of FIG. 20 was a racehorse, shows ten data points within the generally fit condition, and three data points outside. The horse won a race at the time of the study.

Figure 21:
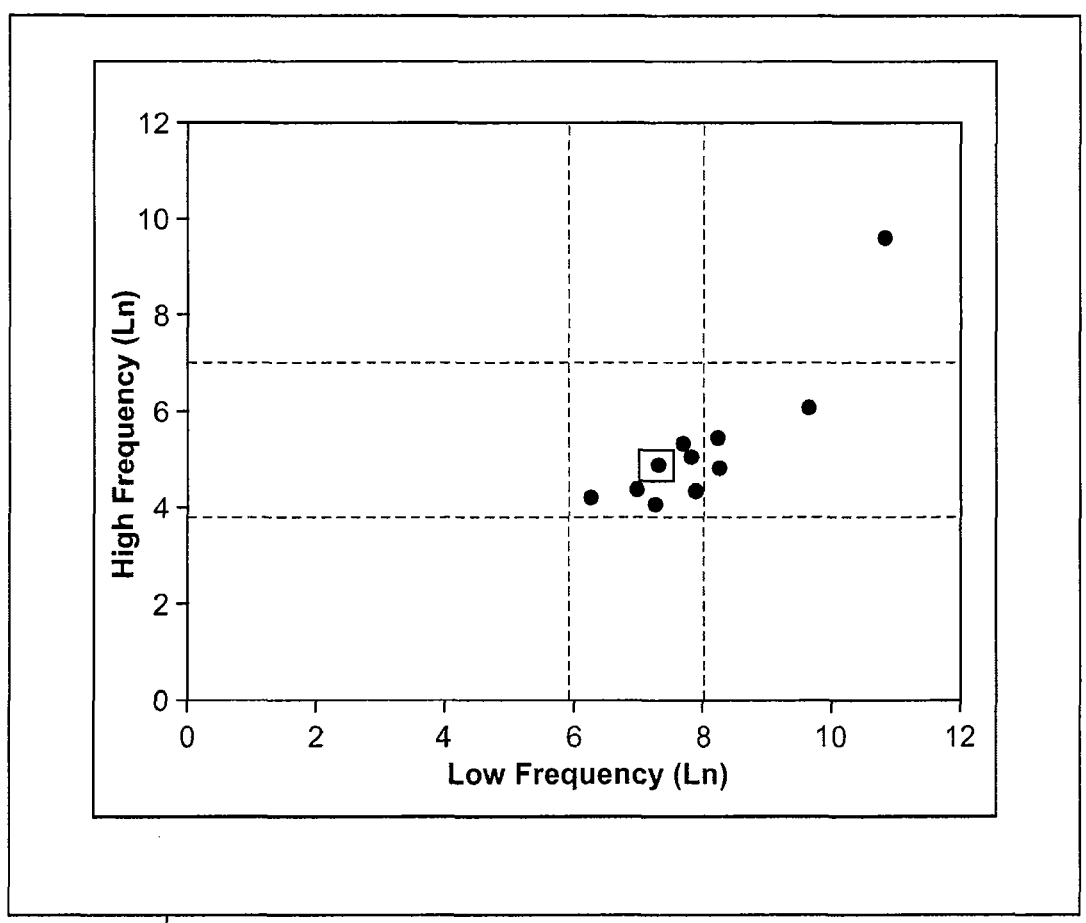
FIG. 21 is an illustration of the autonomic dynamic diagram portion of the report illustrated in FIG. 5 for another animal under study.

FIG. 21 is an illustration of the autonomic dynamic diagram portion 2102 of a condition report such as the report illustrated in FIG. 5 for another animal under study. The FIG. 21 horse was a racehorse that sustained a fracture two months after the data collection, and was withdrawn from training. For the FIG. 21 horse, the number of data points in the generally fit condition (greater than ln(LF)=8.0 and below in(HF)=7.0) is three and the number of data points outside of that condition in the region of ln(HF)=4.0 is seven, a ratio of 3:7. This data (FIG. 21) indicates a fatigue condition and has value as a predictor of impending injury or breakdown.

Figure 22:
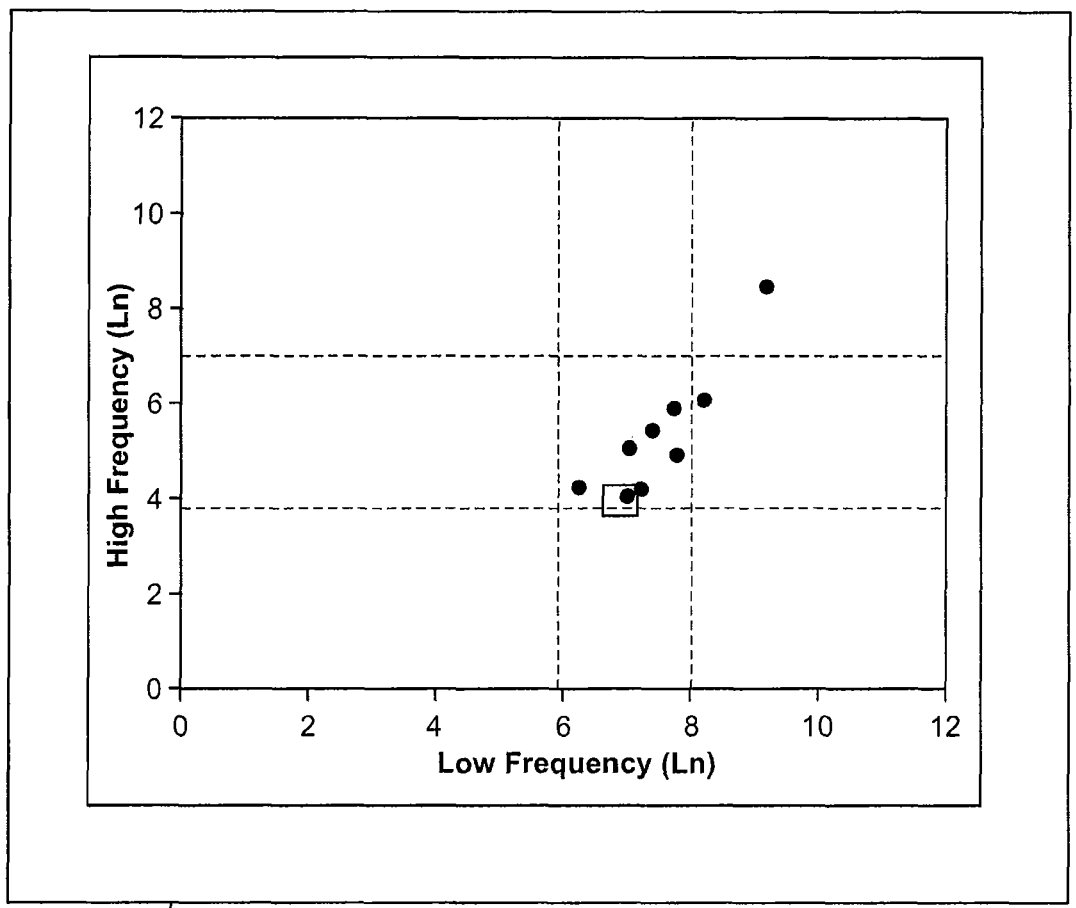
FIG. 22 is an illustration of the autonomic dynamic diagram portion of the report illustrated in FIG. 5 for another animal under study.

FIG. 22 is an illustration of the autonomic dynamic diagram portion 2202 of a condition report such as the report illustrated in FIG. 5 for another animal under study. The horse of FIG. 22 is a racehorse. One data point is in a "stress box" region of the graph (ln(LF)≈8.0 and ln(HF)≈7.0) and one data point is in a "fit" or "ready-to-run" region (ln(LF)≈8.0 and ≈4.0<ln(HF)≈7.0). It should be noted that, for a racehorse, an isolated data point in the "stress" region is not necessarily cause for alarm, as data points in the "stress" region are correlated with anxiety and not necessarily ill health. Moreover, a large number of racehorses are known to suffer from ulcers, and untreated ulcers may result in "stress" region data points. Thus, the horse of FIG. 22 has seven data points in the unacceptable region. Thus, the data for FIG. 22 shows a racehorse that produced data points in an "acceptable" or "ready-to-run" region (for a racehorse) and data points in an "unacceptable" condition at a ratio of 2:7, indicating a fatigue condition. In a racehorse, the present inventor has found that a fatigue condition is a predictor of breakdown, if training is not halted or modified.

Review of data collected from actual horses and correlation with their known condition at the time of data collection, illustrated in Table 1 below, shows the following general guidelines for exemplary classifications of health and condition assessment, given approximate values for x and y data:

TABLE 1

| Condition | ln(LF) x-axis | ln(HF) y-axis |
|---|---|---|
| pain | x > ≈6.0, x < ≈8.2 | y > ≈7.0, y < ≈10.0 |
| stress | x > ≈8.0 | y > ≈7.0, y < ≈12.0 |
| fit ("ready to run") | x > ≈8.5, x < ≈10.4* | y > ≈4.0, y < ≈7.0 |
| general health | x > ≈6.0, x < ≈8.0 | y > ≈4.5, y < ≈6.0 |
| fatigue** | x > ≈6.0, x < ≈10.0 | y > ≈3.0, y < ≈5.0 |
| systemic compromise | x > ≈2.0, x < ≈6.0 | y > ≈2.0, y < ≈5.0 |

*although values greater than about 8.0 generally indicate fitness, values where x > ≈10.5 may indicate a health problem and generally are experienced with pain.
**fatigue is indicated, or "not fit for racing" condition, in the case of a racing thoroughbred or performance horse, for these data values. Fatigue may or may not be accompanied by inflammation, and may or may not be accompanied by depression.

As used herein, "health condition" is a descriptive phrase and is selected from among the categories in Table 1, categories of pain, stress (anxiety), fit, general health (healthy), fatigue, and systemic compromise. These categories, or health conditions, correspond to locations (boxes) on the HF/LF graphs. Thus, a healthy horse with stress or anxiety has a "health condition" of "anxiety", which may or may not be accompanied by a characterization of that horse being "healthy". So a healthy horse with anxiety would show on the "health condition" graph in the particular quadrant for "anxiety" and may also be healthy, or not.

It should be noted that, when racehorses come into training and are becoming more fit, they will often pass through what would be the fatigue area (moving to the right in the graphs) for a horse that is in a ready-to-run state. The "stress" condition indicates a condition in which the animal is experiencing stress without fatigue or systemic compromise, although gastrointestinal (GI) signs may be present, such as pain from uncomplicated gas colic, diarrhea, or Equine Gastric Ulcer Syndrome (EGUS). The stress condition can include an emotional component (e.g., anxiety). Thus, the stress region of the diagram can include characteristics such as stress with emotion (e.g., concern or worry), and/or pain causing anxiety (e.g., simple gas colic), and/or nervousness. The "general health" condition would be a substandard condition ("unacceptable" condition) for a race horse or performance horse, but would be sufficient (acceptable) for a pleasure horse or companion horse. Based on this data classification scheme, the apparatus 102 (FIG. 1) can produce an output comprising an assessment signal for the animal under study. In particular, an animal that receives an assessment of a pain, stress, fatigue, or systemic compromise would be indicated as having a poor health condition. An animal that receives an assessment of fit or general health, would be indicated as having a corresponding condition. If desired, the apparatus may permit a user to make minor adjustment to the threshold values of pain, stress, fatigue, and so forth, to account for individual differences and species differences, as needed. Prior to the test and assessment operation, however, the threshold values would be fixed and predetermined so as to provide a prompt, substantially real-time report assessment for the animal under study, as described above.

It should be noted that the values in Table 1 above have been derived from data collection involving horses. Those skilled in the art will understand that different types of horses (e.g. performance horses as opposed to companion horses) may have different labels associated with the regions of the ln(LF)–ln(HF) graph for IBI data. Similarly, different species of animals (e.g. dogs, cats, birds, fish) may have different labels associated with regions of the ln(LF)-ln(HF) graph for IBI data for their corresponding ranges of data values that indicate the health condition assessment described herein. In this way, the ratio of ln(LF) to ln(HF) for IBI data and related heart rate information as described above provides an indicator or health condition for the animal under study.

Figure 23:
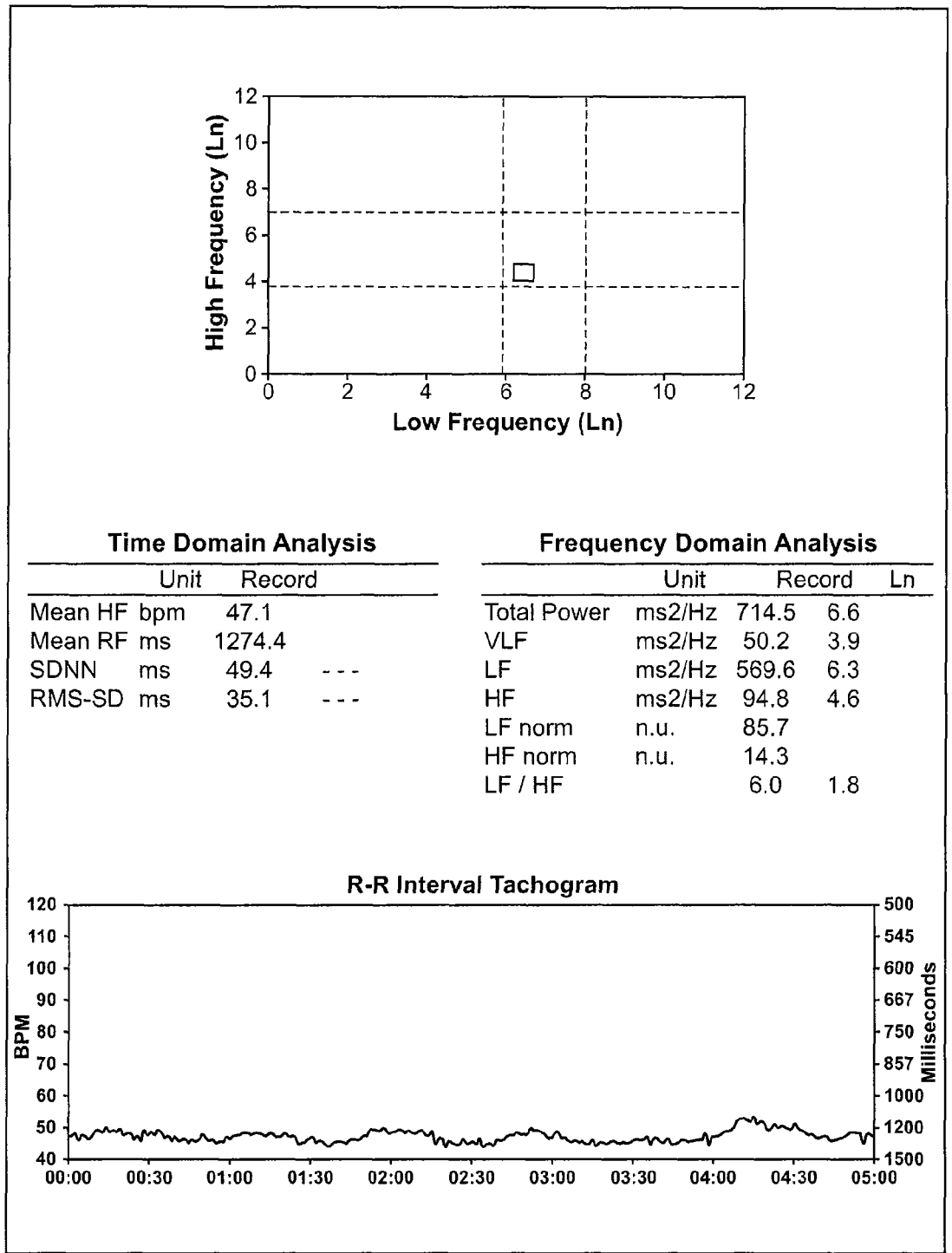
FIG. 23 is an illustration of a health condition report produced by the system illustrated in FIG. 1.

FIG. 23 is an illustration of a portion of a health condition report 2302 produced by the system illustrated in FIG. 1, and shows further details that are produced by the analysis processing and health condition features of the system. The FIG. 23 data was collected from a horse with massive lymphangitis (an infection involving the lymphatic system) in the leg. The infected leg was observed to be extremely swollen and the horse was in obvious pain. The data of FIG. 23, on casual observation, might not otherwise indicate that the horse is in pain (note the location of the data relative to the "pain" box). Nevertheless, the collected data, and the health condition report produced by the system, show rapid and repetitive accelerations and decelerations resulting in a "spikey" appearance of the tachogram, which could be experienced as a shooting pain, and would indicate a pain condition. The data shows that the horse is compromised from the massive infection (SDNN=49 and TP=714.5). This data indicates an ill, systemically compromised horse in pain. Thus, although the horse of FIG. 23 would not be categorized into the "uncompromised pain box" described above in Table 1, the system would produce a health condition report indicating that this horse in a pain condition, from detecting the pain-indicating tachogram data that was collected. The graph of FIG. 23 can be compared with the other cases of the foot abscess (FIG. 8) and submandibular abscess (FIG. 9); in both those other cases, it appears the infection is isolated into an abscess and has not compromised the horse systemically. That is, the autonomic dynamic report indicates the animals are not systematically compromised. Hence, those horses are categorized in the uncompromised pain box.

In accordance with the techniques described herein, an animal state metric indicative of health condition is determined, such as the health condition assessment characterizations described above. The animal state metric indicates health condition and comprises a set of numerical parameters that are correlated to a clinical assessment of pain, stress, degree of athletic fitness, fatigue, and systemic compromise for the animal. As described above, the parameters include HF/LF ratio, total power, and so forth, as presented in the illustrations and accompanying description.

As noted above, a wide variety of devices can be provided as part of the data processing apparatus. For example, communications from the heart rate sensors (FIG. 1) can take place with devices that can themselves provide data collection, data store, data analysis, and data reporting. For example, notebook computers typically have sufficient resources to perform all of these functions in real time, by receiving the data from the heart rate sensors, storing the data in on-board storage, performing data analysis, and producing the health condition report and showing it to the user via the notebook computer display. The keyboard and associated keys of the notebook can be utilized for user commands and data input operations. Other devices such as personal digital assistants (PDAs) also can have sufficient resources to provide all such functions, in real time. Alternatively, multiple independent devices can provide the various functions in real time. The devices may include network devices such as smart telephones and PDA's with network communications capabilities. As noted, integrated devices with appropriate subsystems may be able to non-invasively collect the data from the animal, such as by infrared (IR) detection of heart beat information, and such devices can then perform the data collection and analysis necessary for assessment, and then can provide the report to the user for the animal under study. Alternatively, data collection and analysis can be performed at network devices specially constructed for the purpose, with which a subsystem of the data processing apparatus 102 communicates. An example of such a system is illustrated in FIG. 24.

Figure 24:
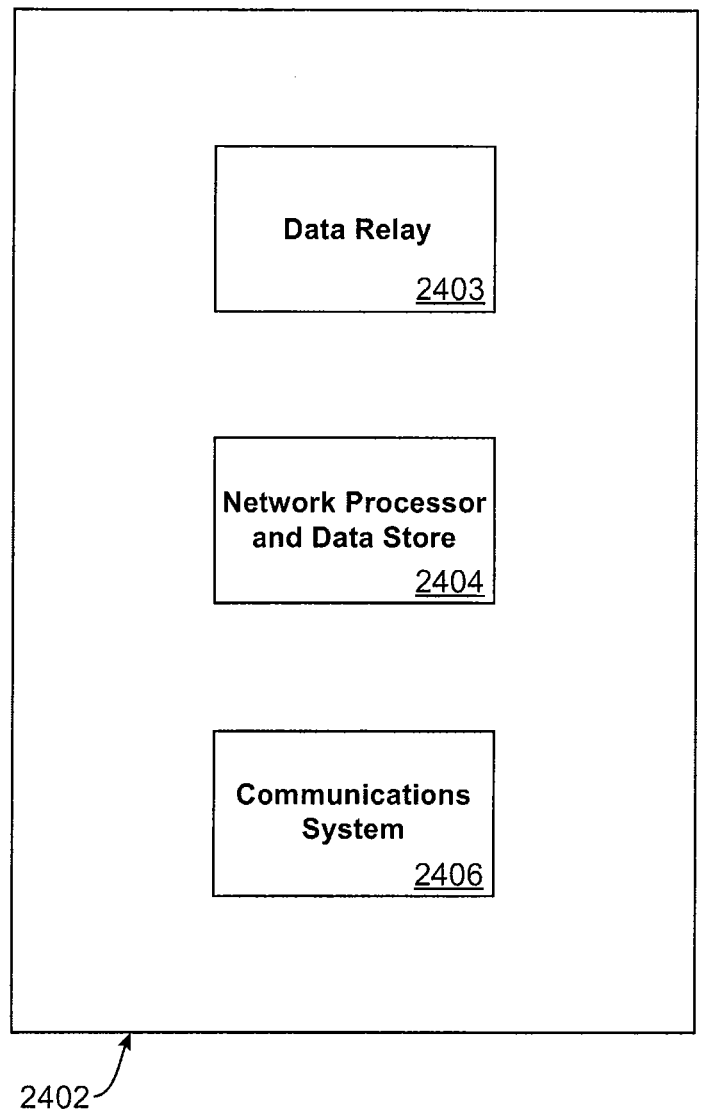
FIG. 24 is a block diagram of an alternative system that performs heart rate variability processing.

FIG. 24 is a block diagram of an alternative system with a data processing configuration 2402 having independent devices, each of which performs a different segment of the heart rate variability processing as described above. The FIG. 24 configuration can also support additional processing features. In FIG. 24, a data relay unit 2403 receives heart rate and/or IBI data of the animal from the sensors 108 (FIG. 1). The data relay unit provides the heart rate and/or IBI data to a network processor and data store 2404. The relay unit 2403 can store the received heart rate and/or IBI data in memory or can simply store portions of the data temporarily in a data buffer before streaming the buffered data to the network processor 2404. Because the relay unit 2403 need only collect data and perhaps only for purposes of streaming, its resource requirements can be more modest as compared to the single integrated device alternative described previously. For example, the relay unit 2403 can comprise a network interface device that collects data from the animal sensors and provides the data (e.g. by streaming) to a network for processing at a remote processor.

The network processor and data store 2404 can comprise a network server that receives the collected heart rate and/or IBI data and provides HRV data analysis and health condition determination in real time. The network server 2404 can be located, for example, on a network node of the Internet or of a local area network in close proximity to the data relay unit 2403. The data can be transferred between the relay unit 2403 and the network server 2404 by means of wireless data communication, just as the case with the transfer of data from the sensors 108 and data processing apparatus 102 of FIG. 1, or the data transfer can occur over a wired connection. For example, with respect to FIG. 24, the data communication between the sensors and the data relay unit 2403 can occur over a Bluetooth wireless link. The data communication between the data relay unit 2403 and network server 2404 can occur over a telecommunications link where, for example, the data collection unit comprises a smart telephone or PDA that can transfer data over Bluetooth links or over telephone telecommunication data links, and the network server comprises a network computer that is connected to the Internet and can receive data from a variety of data devices. The network server can then communicate with a communications system 2406, such as the public switched telephone network or other communications systems. The communications system enables communication with designated parties, such as a care giver, veterinarian, owner, or other persons. Thus, a notification or an emergency message can be delivered from the network server 2404 to appropriate persons through the communications system 2406.

With the system of FIG. 24, for example, a sensor pack 102 can be attached to an animal under study so that heart rate and/or IBI data of the animal can be transmitted wirelessly and received at a data relay unit 2403, such as a smart telephone or PDA device of an attending health care worker. The data relay unit can then transmit data (either the raw heart rate and/or IBI data or processed data or health condition data) to another device, such as a network processor. If the data relay unit 2403 has sufficient computing power to process the heart rate and/or IBI data and generate a health condition signal (such as a warning signal or a health approval signal), then the data relay unit can provide an indication such as a warning tone or approval tone or visual display. The data can then be transmitted to a network server 2404 for archival or other recording purposes. In addition, a warning symbol or health approval signal can be dispatched via the communications system 2406, such as by providing a text message to a predetermined emergency telephone number or providing an email message to a predetermined contact address, or a combination of all these.

Figure 25:
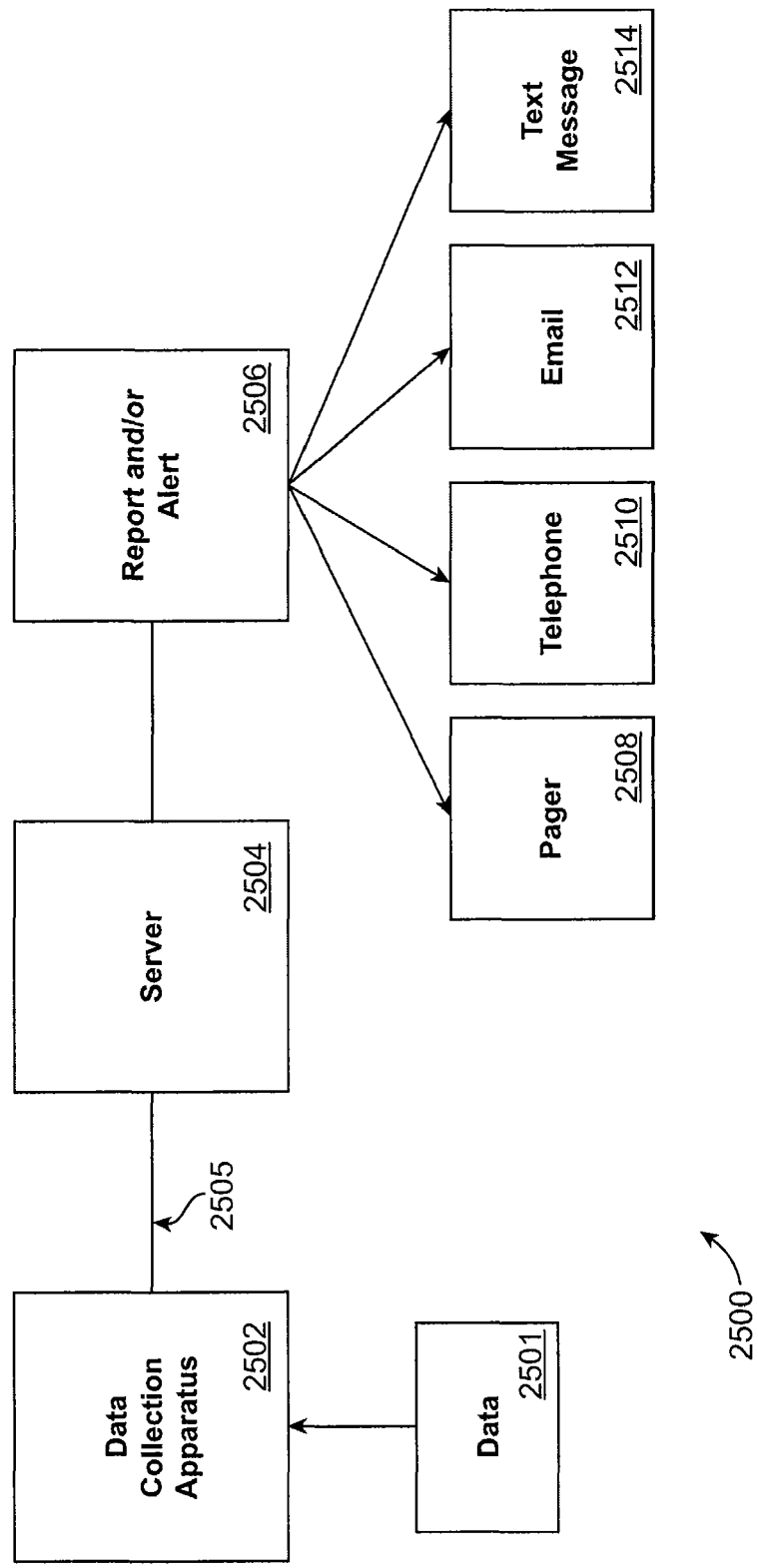
FIG. 25 is a block diagram of a system that implements health condition data collection and monitoring in accordance with the invention.

FIG. 25 is a block diagram of a system 2500 that implements health condition data collection and monitoring in accordance with the invention. The FIG. 25 system is configured for convenient remote monitoring of animal condition. Data 2501 is received from the animal under study at the data collection apparatus 2502. The data collection apparatus 2502 can comprise a hand-held unit that can determine heart beat information even in the absence of physical contact with the animal, or the data reception at the apparatus can occur in conjunction with data transmission from sensors attached to the animal or implanted in the animal or ingested by the animal. For example, the heart rate information might be received by the data collection apparatus 2502 from infrared detection or acoustic detection or visual detection of animal characteristics without any sensor attachment or implantation to the animal. Alternatively, sensors with telemetry might be attached or implanted to the animal and may send the heart rate information directly to the apparatus 2502. Alternatively, the sensors may comprise the sensor apparatus 108 illustrated in FIG. 1. As noted, the presence of sensors on or within the animal for heart beat information monitoring should not disturb or annoy the animal during the data collection process.

Once the data is collected at the data collection apparatus 2502, the data can be forwarded or streamed to a server 2504 for analysis and reporting, or the apparatus itself can perform the analysis and forward the results to the server for delivery. The connection 2505 between the data collection apparatus 2502 and the server 2504 can be wired or wireless, such as by telephone modem connection, Internet communications, satellite communications, local connection (e.g., Bluetooth specification communications), or the like. The server 2504 has sufficient resources for data analysis (if analysis is not performed by the data collection apparatus) and for network communication with an end user or customer. Moreover, as noted above, at the point of report generation, data relating to a "known good health" animal, either the very same animal as that under study or a similar animal, is needed so as to ensure valid data analysis. If desired, the server can store or retrieve such "known good health" data within integrated data storage or from network data storage.

When the server has generated a report or alert message as a result of the data analysis, the server will send a report or alert message 2506. The report or alert message comprises a health condition signal which can be an audible tone, a visual indication, text message, voice message or the like. To ensure a valid report or alert, it is necessary to associate the proper conditions or outcomes to the collected heart rate information. For example, the regions of the ln(LF)-ln(HF) IBI graph such as described above must be associated with the proper labels ("stress", "fit", "fatigue", etc.) for the animal under study. Such distinctions can also be important with respect to data review and edit operations. Therefore, the system 2500 must be configured for a particular animal species and/or type. The system can be configured to a predetermined species and/or type (such as performance horse or companion horse), or the system can receive a user input during a configuration operation of the system via a user keypad or input panel to indicate which particular animal species and type is to be used in determining the report conditions and thereby fixing report parameters ("stress", "fit", "fatigue", etc.) associated with the heart rate information for the animal under study and in performing any data review and edit operations on the collected data. The report or alert message 2506 will be generated in accordance with the description above. Thus, the animal's actual and predicted health condition and performance potential will consider the collected data and the ECG, tachogram, and ln(LF)-ln(HF) data as described above in conjunction with the illustrative data of FIGS. 5-23 and Table 1.

The report or alert message 2506 is sent to a receiving device at a designated destination address, such as a pager message 2508, telephone message 2510, email message 2512, text message 2514, or the like. If desired, the system 2500 can provide a menu of options from a system configuration display by which a user can specify a message hierarchy, in which a designated means of communication is tried first, followed by a designated order of communication means in order. Thus, a telephone pager message 2508 might be desired in the first instance, followed by a telephone message after a predetermined wait interval for acknowledgement, followed by the next specified communication means, and so forth. Such services can be maintained and managed as part of a subscription service, which can permit agreed upon communications and privacy rules to be enforced, as well as data storage and archive options and enhanced data analysis options. In this way, an animal monitoring service using the techniques and data analysis described herein can be implemented that will be easy to use and can provide real time animal condition reports to alert veterinarians, animal health care workers, and concerned animal owners as to the condition of relevant animals that are the subject of the subscription service.

The devices described herein, such as the devices illustrated in FIGS. 1-3 and FIGS. 24-25, shall be understood to comprise devices that include computing processors and other resources (e.g. communications and input/output) sufficient to perform their described functions. For example, the server 2504 may comprise a conventional computer server device capable of network communications using a variety of data protocols, and the data collection apparatus 2502 may comprise a variety of computer devices, including laptop computers, PDAs, Web-enabled cellular telephones, and the like capable of network communications with servers.

The processing described herein is based on extensive data collection activities associated with animals under care. In particular, data studies have been performed with a relatively large population of horses trained for racing, because such animals are genetically similar, relatively the same age, generally at peak performance, and are also subject to severe demands on performance, making them excellent subjects for study. Such studies have formed the basis for the processing described herein.

One feature that can be provided in accordance with the invention is to provide a device and method that enables a veterinarian or other animal health care provider to accurately, conveniently, and efficiently assess pain and well being in animals and for diagnosis of disease conditions and for clinical evaluation of efficacy of therapeutic measures to eliminate or manage such conditions.

It is another feature to provide a device and method for assessment and management of stress in animals, especially animals reared in confinement housing, e.g., a feeder swine or poultry laying house operation.

Another feature is to provide a device and a method for enclosure evaluation for animals reared in or otherwise contained in confinement housing e.g., for determination of optimal breeding conditions (especially for exotic and endangered animal species).

It is a also a feature to provide a device and method for assessment and management of stress in animals, especially for companion animals, e.g., stress levels in pets exposed to separation anxiety.

Yet another feature in accordance with the invention is to provide a device and method which enables real time assessment of aerobic fitness and/or exercise conditioning in athletic animals, e.g., in racing animals such as dogs and horses.

A further feature of the invention is to provide a device and method enabling biofeedback of HRV as a tool to train animals through Pavlovian conditioning to positively influence the autonomic nervous system, e.g., to train an animal to calm itself thereby reducing stress, and/or to manage unacceptable behavioral vices such as cribbing, weaving, barking and the like.

An additional feature of the invention is to provide a device and method for localization of pathologic lesions or a source of pain, e.g., for diagnosis and localization of a lameness producing lesion.

In one embodiment, the present invention provides a method for detection of a preselected condition such as e.g., subclinical stress or subclinical pain in a subject animal using heart rate variability analysis. In one embodiment, the method comprises the steps of determining a heart rate and/or inter-beat interval for the subject animal over a preselected period of time to determine the subject animal's heart rate and/or IBI data. The heart rate and/or IBI data can be detected and analyzed from an ECG or PPG signal received from a signal detection means located on the animal. The method further comprises analyzing the collected heart rate or inter-beat data from the subject animal via spectral analysis to identify a set of heart rate variability data for the subject animal for a selected heart rate variability parameter such as a frequency domain or time domain parameter such as LF/HF ratio. The heart rate variability data from the selected animal can be compared to substantially normal values established for the selected animal species or compared to the subject animal's own previously identified substantially normal values or HRV pattern over a period of time and thereby determine whether the preselected condition exists.

In another embodiment, the invention provides a device and method enabling biofeedback of HRV as a tool to train animals through Pavlovian conditioning and/or rewarding approximations, to positively influence the autonomic nervous system, e.g., to train an animal to calm itself thereby reducing stress, and/or to manage unacceptable behavioral vices such as cribbing, weaving, barking and the like.

Additional objects, advantages and other novel features of the invention will be set forth in part in the description that follows and in part will become apparent to those skilled in the art upon examination of the foregoing or may be learned with the practice of the invention. Additionally, throughout this document, various publications and patents have been cited, the contents of which are incorporated herein by reference in their entirety.

Set forth in greater detail below are specific details related to novel devices and methods for utilizing heart rate variability analysis in animals. In particular, the present invention provides specific teachings related to novel devices and methods for collection of and analysis and utilization of heart rate variability data in animals to diagnose and/or prevent disease or to monitor and/or improve the state of well being in the subject animal. The examples set forth herein are in no way intended to limit the scope of the invention. Those of skill in the art will realize that, given the teachings provided herein, many variations of the methods are possible that will fall within the scope of the invention.

Briefly, in one embodiment, the device of the invention comprises a means for detection of electrical activity of the heart such that heart rate and/or inter-beat intervals can be accurately determined. The heart rate detection means can range from a standard externally applied electrocardiographic recording device designed for use in detecting and reproducing an electrocardiogram (ECG) signal generated from the heart, e.g., a Holter system similar to the type set forth in Bowen, M., "Heart Rate Variability", Cardiology of the Horse, Ch. 11: 161-76, (1999) W.B. Saunders. Although many devices currently exist which can provide means for detection of the electrical activity of the heart, one important feature of the detection means of the instant invention is in the accurate detection of the QRS complexes and, in particular, the R wave component of the signal such that an accurate R-R interval can be ascertained by algorithmic or other analysis of the detected signal.

Alternatively, heart rate and inter-beat time intervals can be detected via utilization of a signal detection means which measures peripheral blood flow to the extremities such as a photoplethysmograph (PPG) or pulse wave sensor. Briefly, the PPG utilizes a photocell which converts light into electrical energy. A beam of infrared light is projected through a selected body tissue and toward the photocell. The amount of light reaching the photocell is inversely proportional to the amount of blood within the tissue and can be used to record these changes which reflect heart rate and inter-beat intervals similar to the inter-beat intervals of the ECG. One of skill in the art can appreciate that the heart rate or signal detection means can be removably attached to the subject animal or can be implanted at a desired location within the animals body, e.g., subcutaneously or internalized via swallowing or oral ingestion of the signal detection means as set forth in certain of the telemetric monitoring systems referenced herein.

Associated with the heart rate detection means is a means for recording or storing the detected ECG or PPG signal. The recording means can be selected from among any of a number of commercially available units. Alternatively, the detection means and recording or data storage means and can be incorporated into the a single device which detects and records the ECG or PPG signal. ECG or PPG signal recordings can be analog or digital and can be recorded as with e.g., the Holter system or pulse wave sensor, or transmitted from the detection means via, e.g., radiotelemetry directly into a remote recording device where the signal is stored and/or analyzed via commercially available software, e.g., from Biocom Technologies, Poulsbo, Wash., USA (see, e.g., the Web site at www.biocomtech.com).

As set forth more fully herein and as can be appreciated by one of skill in the art, algorithmic software for spectral analysis of the detected ECG or PPG signal can be modified or adjusted or otherwise adapted to suit the species or subject animal of interest. For example, the human HRV variability analysis software available from Biocom Technologies can be modified or adapted for use in analysis of HRV data in a selected species of animal, e.g. for use on a horse or dog (see, Pougatchev, Vadim et al.; BIOCOM HEART RHYTHM SCANNER USERS MANUAL, "Heart Rate Variability Analysis System Users Manuel, Version 2.0"; available at URL of www.biocomtech.com, the contents of which are hereby incorporated herein by reference). Briefly, data (ECG or PPG signals) can be collected for a preselected period of time from a pool of substantially normal and unstressed animals. The collected data can be analyzed via spectral analysis to establish substantially normal values and ranges for any of a number of selected variables of time domain or frequency domain such as high frequency (HF) or low frequency (LF) signals of the recorded signal as set forth more fully below. For example, ranges for normal LF and HF of the recorded ECG signals can be established for the species of interest. See, e.g., Ohmura et al, "Effects of Atropine Injection on Heart Rate Variability in Thoroughbred Horses" J. Vet. Med. Sci. 63(12): 1359-1360 (2001) which cites one set of normal HF and LF power ranges. These normal ranges can then be used for comparison and/or analysis HRV data collected from a subject animal of the selected species for use in the methods set forth herein, e.g., for use in a method of evaluation of stress or fitness evaluation and the like.

A variety of commercially available telemetry systems are available which utilize external as well as internal signal detection means (transmitters) and, depending upon the selected animal, can be modified, or otherwise adapted for use in the methods set forth herein. Examples of telemetry monitoring systems include the externally applied monitor and telemetry acquisition systems "Research Model" from Polar Heart Rate Monitors (www.horsebeat.co.uk), the implantable data and telemetry acquisition systems from Data Sciences International (DSI.TM.; www.datasci.com) and Lotek Wireless Inc. (www.lotek.com) or NASA telemetry monitoring systems (www.nasa.gov) and the like. In a preferred embodiment, the invention provides a noninvasive telemetric device for small animals that (e.g., companion animals such as dogs and cats) is conducive to home use (e.g., a collar-type device) for, e.g., out patient monitoring.

The collected ECG or PPG signal can be analyzed for a preselected period of time utilizing a variety of parameters including but not limited to: time domain parameters such as heart rate (mean heart rate averaged over a selected time, beats per minute (BPM)); mean NN which is a mean inter-beat interval value averaged over the preselected period of time; and the SDNN which is a standard deviation of the NN intervals derived from calculating the square root of their variance. The collected ECG or PPG signal can likewise be analyzed for a preselected period of time utilizing a variety of frequency domain parameters including, but not limited to: the total power (TP), very low frequency signals (VLF); low frequency signals (LF); high frequency signals (HF); LF/HF ratio which measures the overall balance of the autonomic nervous system between the sympathetic and parasympathetic components; and normalized values for high and low frequency. The HF and LF components of the spectral analysis can be used in a comparison over the duration of the preselected recording time (e.g. a 5-10 minute recording or a 24 hour Holter-type recording) to determine the overall balance of the autonomic nervous system, e.g., the relative amount of HF signal to LF signal. This balance profile can also be compared with the SDNN to determine the relative total power or robustness of the autonomic nervous system for the selected animal.

The present invention provides a method of assessing HRV in a selected animal utilizing one or more of the above-described parameters which will enable a veterinarian to accurately, conveniently and efficiently assess, e.g., pain and/or the well being in animals, for diagnosis of disease conditions and for clinical evaluation of efficacy of therapeutic measures to eliminate or manage a particular condition. One of skill in the art can appreciate that, given the teachings set forth herein, the devices and methods can be readily adapted to include any of a number of selected animal species including, but not limited to, horses, dogs, cats, cows, pigs, chickens, sheep, goats and other domestic livestock or companion animals. The devices and methods set forth herein are also meant to be adaptable for and to include exotic animal species and aquatic or marine animals as well as laboratory animals and other animals reared or housed in confinement. In addition, telemetrically monitoring sentinel animals in wild animal preserves and monitoring environmental changes and impact on ecosystems via sentinel animals in the wild are also contemplated.

In one embodiment of the invention, a method for detection of pain in a preselected animal is provided which is comprised of establishing a normal R-R interval and/or other HRV data and/or indices from the preselected animal (or a predicted normal HRV for the animal species); monitoring the HRV of preselected animal for changes in HRV which are indicative of pain. In general, an animal under the influence of a painful stimulus will elicit changes in HRV, e.g., a change in R-R interval and/or other HRV indices such as an increase in LF power output which is indicative of the effect of a painful stimulus and sympathetic output in response to the pain.

While not wishing to be bound by any particular theory, in humans, e.g., when the parasympathetic system is dominant, the heart inter-beat levels (IBI) are oscillating with higher frequency (e.g., 0.15-0.4. Hz). When sympathetic arousal occurs, the lower frequency oscillations take place. The low frequency range (e.g., 0.4-0.15 Hz) of the IBI power spectrum displays sympathetic influence. The low frequency/high frequency ratio is used to show the balance between both branches of the autonomic nervous system. Given the teachings set forth herein, the response and optimal balance which is species specific can be determined for the selected animal species and a subject animal then monitored accordingly.

The method further can comprise identification of the etiologic agent which is responsible for the pain in the selected animal and attenuating and/or removal of the etiologic agent or treatment with a suitable drug or other therapeutic modality to reduce the level of pain seen in the animal via continued monitoring of HRV status. Real time HRV can be monitored before, during and after specific therapies to determine therapeutic efficacy. Subsequent HRV readings would indicate the long term efficacy and lasting effects of therapeutic or ameliorative treatment measures.

For example, a selected animal's HRV could be monitored (e.g., postsurgically) to determine pain levels and thereby dictate administration of pain medication and case management. In addition, e.g., as an adjunct in lameness diagnosis and treatment, in conjunction with clinical examination, flexion tests, palpation, manipulation, and movement, real time HRV fluctuations can be used to indicate pain and/or stress response in the selected animal (patient) in response to specific clinical diagnostic measures. Assessment of HRV fluctuations can also be used as an adjunct in the diagnosis of neuropathy. HRV can be monitored in conjunction with clinical examination (e.g., tapping or balloting a site of suspected injury, then comparing HRV fluctuation to this same function performed on a clinically normal limb).

Given the teachings set forth herein, HRV can also be used as an adjunct in the localization of other pathologic lesions. Pain and/or stress response monitored via HRV during clinical examination, palpation and movement could assist in localization of pathologic lesions. For example, 24 hour readings or another selected time interval can be used to correlate pain and stress associated with specific events (e.g., swallowing, gastric filling, urination, specific movements and the like).

The present invention also provides a method for collection and assessment of HRV data in animals for management of stress levels in animals, especially animals reared in confinement housing, e.g., as a means for enclosure evaluation and environmental management of a preselected confined animal or group of animals, e.g., to increase production. The devices and methods set forth and provided herein are meant to include any animal that can be housed in a confinement situation and can include, e.g., enclosure of animals used in food production, breeding operations, quarantine and/or zoo-like settings, habitats, and the like.

As used herein, the term "stress" is meant to include, but not be limited to the effect seen from the exertion or application of any external and/or internal stimuli which exerts a negative effect or other wise negatively influences the health status of the subject animal. Specific examples of such stress factors include, e.g., prolonged exposure to unfavorable environmental conditions such as extreme temperatures, over crowding, loud noise, electrical or electromagnetic fields, separation from a companion animal or from an owner, removal from a familiar environment, shipping transport, athletic competition and the like. Other examples of stress related monitoring embodied by the invention include enclosure evaluation and determination of optimal breeding conditions for animals, especially exotics and endangered species as well as determination of well-being of performance and exhibit animals (e.g., circus animals and animal exhibits at zoological parks).

One embodiment of the method for management of stress in a selected group of animals, e.g., a herd or flock, comprises identification of at least one or more sentinel animals from within the herd, establishing a normal R-R interval, LF/HF ratio to show balance between both branches of the autonomic nervous system, or other HRV, data for the sentinel animals and monitoring the sentinel animals for changes in HRV which are indicative of stress. The method can further comprise identification of the etiologic agent which is causing stress in the sentinel animal and attenuation of the etiologic agent to reduce the level of stress seen in the sentinel animal.

For example, in domestic, exotic, marine, and food animals HRV measurements can be used to evaluate stress levels. Optimal HRV values for the selected animal species can initially be determined, e.g., via parallel cortisol studies. Given the teachings set forth herein, HRV can be used as an informative method for evaluation of mental stress and fatigue. In production animals, optimal HRV values can be used to correlate with optimal weight gain and/or rate of production and appropriate measures taken to maintain a selected optimum HRV level in sentinel animals.

Real time HRV measurements can then be used to identify and evaluate the etiologic factors that cause or produce stress in the selected animal species and also to identify factors which relieve or reduce the stress. Given the teachings and methods set forth herein, HRV monitoring has the capability to give animals a "voice" with respect to their pain and stress status (i.e., as an advocate and conduit for animals to communicate their pain and stress).

In one embodiment of the invention, a method for monitoring stress associated with separation anxiety is provided. A home HRV monitoring unit can be provided, e.g., for household pets, whereby HRV fluctuations would indicate stress levels (e.g., separation anxiety) and then the unit can be used to trigger changes in the environment to reduce stress (e.g., turning on music, activating a sound or other vibration, activating a recording of the animal owner's voice, notification of the veterinarian or other caretaker as to an outpatient's status, or a call to the animal owner's cell phone and the like).

Another embodiment of the invention provides a method for enabling biofeedback of HRV as a tool to train animals through Pavlovian conditioning to positively influence the autonomic nervous system, e.g., to train an animal to calm itself thereby reducing stress, and/or to manage unacceptable behavioral vices such as cribbing, weaving, barking and the like. Animals could be trained to calm themselves or reach a desirable HRV value by rewarding the animal with a stimulus (e.g., click) and a treat when desirable HRV values are approached or reached. Eventually, the animal would only need the stimulus to achieve the desired result (e.g., calming or sedation). This would have many applications in performance animals. This technique could also be used to manage stable vices (e.g., cribbing and weaving). Stalls could be fitted with automatic devices that reward the animal when desirable HRV values are achieved.

The features that can be provided in accordance with the present invention include:

(1) A method for detection of a preselected condition in a subject animal from a preselected animal species using heart rate variability analysis comprising the steps of: (a) Determining a heart rate for the subject animal over a preselected period of time to determine the subject animal's heart rate data; and (b) Analyzing the determined heart rate data from the subject animal to identify the subject animal's heart rate variability data for a selected heart rate variability parameter and thereby determine whether the preselected condition exists.

(2) The method of (1), wherein prior to the analyzing step the method further comprises the step of establishing a substantially normal range of values for the selected heart rate variability parameter for the preselected animal species.

(3) The method of claim (1), wherein the determined heart rate data is analyzed via a spectral analysis to determine heart rate variability data for at least one selected heart rate variability parameter (4) The method of (3), wherein the selected heart rate variability parameter is selected from the group consisting of a frequency domain parameter and a time domain parameter.

(5) The method of (4), wherein the selected heart rate variability parameter is a time domain parameter selected from the group consisting of: heart rate (HR); mean inter-beat interval (NN); standard deviation of the inter-beat interval (SDNN); and the square root of the mean squared differences of successive inter-beat intervals (RMS-SD).

(6) The method of (5), wherein the selected heart rate variability parameter is a frequency domain parameter selected from the group consisting of: total power (TP); very low frequency (VLF); low frequency (LF); high frequency (HF); low frequency to high frequency ratio (LF/HF ratio); normalized low frequency (LF norm); and normalized high frequency (HF norm).

(7) The method of (2) further comprising the step of comparing the substantially normal range of values for the selected heart rate variability parameter for the preselected animal species to the analyzed heart rate variability data for the selected heart rate variability parameter of the subject animal.

(8) The method of (1), wherein prior to the analyzing step the method further comprises the step of establishing a substantially normal range of values for the selected heart rate variability parameter for the subject animal.

(9) The method of (8), further comprising the step of comparing the substantially normal range of values for the selected heart rate variability parameter for the subject animal to the analyzed heart rate variability data for the selected heart rate variability parameter from the selected animal.

(10) The method of (1) wherein the preselected animal species is selected from the group consisting of: canine, feline, ovine, equine, bovine, caprine, and avian.

(11) The method of (1), wherein the preselected animal species is an exotic animal species.

(12) The method of (1), wherein the preselected animal species is a fish.

(13) The method of (1), wherein the preselected animal is an animal in captivity or confinement.

(14) The method of (1), wherein the preselected condition is stress.

(15) The method of (1), wherein the preselected condition is pain.

(16) The method of (14), wherein an etiologic agent producing stress is identified and substantially attenuated or removed from the subject animal to thereby substantially eliminate stress in the subject animal.

(17) The method of (14), wherein an etiologic agent producing pain is identified and substantially attenuated, removed or a therapeutic administered to the subject animal to thereby substantially eliminate pain in the subject animal.

(18) The method of (1), wherein prior to the analyzing step the method further comprises recording the determined heart rate data of the subject animal for the preselected period of time.

(19) The method of (1), wherein prior to the analyzing step the method further comprises the step of establishing an expected range of values for the selected heart rate variability parameter for preselected condition when present in the preselected animal species.

(20) The method of (1), wherein the animal is a preselected sentinel animal in a group of animals.

(21) The method of (1), wherein the preselected condition is a subclinical condition.

(22) The method of (1), wherein the preselected period of time is from between about 15 seconds to about 20 minutes, but is especially about 10 minutes.

(23) The method of (1), wherein the preselected period of time is from between about 6 hours and about 36 hours, but is especially about 24 hours.

The foregoing description of preferred embodiments has been presented for purposes of illustration and description. It is not intended to be exhaustive or to limit the invention to the precise form disclosed. Modifications or variations are possible in light of the above teachings and will occur to those skilled in the art. The embodiments set forth herein were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

I claim:

1. A method of operating a processor for assessing health condition of a non-human animal from a preselected animal species under study, the method comprising:

receiving heart rate information at the processor from the non-human animal under study over a wireless communication link until sufficient data has been collected for reliable health condition assessment;

performing heart rate variability (HRV) analysis by the processor on the received heart rate information for determining autonomic dynamics of the animal under study with respect to a species of which the animal under study is a member, wherein the HRV analysis relates to time domain HRV data and frequency domain HRV data of the received heart rate information that are evaluated with respect to physiological states and corresponding health condition for the time domain HRV data and frequency domain HRV data for the species of the animal under study;

generating a health condition report by the processor for the animal under study based on a plurality of data values generated from the HRV analysis such that the data values are substantially within a range of numerical magnitude that corresponds to a predetermined health condition report characterization of the animal under study, wherein the characterization indicates whether the animal under study is fit for physical exertion;

wherein the received heart rate information includes data that provides accurate information relating to heart rate and heart interbeat interval (IBI) of the animal species under study.

2. The method as defined in claim 1, further including:
receiving the heart rate information from the animal under study when the animal is in a known healthy condition;
storing the data at a data store for later comparison.

3. The method as defined in claim 1, further including:
receiving heart rate information that comprises data sufficient to establish a baseline of heart rate variability data for one or more animals similar to the animal under study who are in a known healthy condition.

4. The method as defined in claim 1, wherein performing heart rate variability analysis comprises:
determining standard deviation data for variation between heart beats of the received heart rate information;
determining high frequency (HF) and low frequency (LF) components of the received heart rate information; and
determining a plot of the HF and LF components and identifying quadrants of the plot that correspond to predetermined health condition states;
determining a value for total power output of the animal under study.

5. The method as defined in claim 4, further including:
indicating an unhealthy condition of the animal under study if at least one data point of the plot exceeds a predetermined value.

6. The method as defined in claim 4, wherein the health condition report includes a representation of a log-log plot of the HF and LF components.

7. The method as defined in claim 1, wherein generating a health condition report comprises:
transmitting a health condition signal over a wireless communication link to a receiving device.

8. The method as defined in claim 7, wherein the receiving device comprises a processing device that communicates with a computer network.

9. The method as defined in claim 8, wherein the receiving device comprises a portable processing device with an integral display that indicates the health condition signal.

10. The method as defined in claim 1, wherein performing heart rate variability analysis comprises:
transmitting the received heart rate information to a network processor;
comparing the received heart rate information at the network processor against corresponding heart rate information for known healthy condition animal; and
determining health condition of the animal under study in response to the comparison.

11. The method of claim 1, wherein the received heart rate information comprises data that provides accurate information relating to R wave component data of the heart rate information for the animal species under study.

12. The method as defined in claim 1, wherein the health condition report characterization is one of a plurality of characterization categories.

13. The method as defined in claim 12, wherein the characterization categories include at least a category that indicates general health and a category that indicates systemic compromise.

14. A system for assessing health condition of a non-human animal from a preselected animal species under study, the system comprising:
a data collection unit that is configured to receive heart rate information from the non-human animal under study until sufficient data has been collected for reliable health condition assessment;
a data analysis unit that is configured to process the received heart rate information and is configured to perform heart rate variability (HRV) analysis on the received heart rate information for determining autonomic dynamics of the animal under study with respect to a species of which the animal under study is a member, wherein the HRV analysis relates to time domain HRV data and frequency domain HRV data of the received heart rate information that are evaluated with respect to physiological states and corresponding health condition for the time domain HRV data and frequency domain HRV data for the species of the animal under study; and
a data reporting unit that is configured to generate a health condition report for the animal under study based on a plurality of data values generated from the HRV analysis such that the data values are substantially within a range of numerical magnitude that corresponds to a predetermined health condition report characterization of the animal under study, wherein the characterization indicates whether the animal under study is fit for physical exertion;
wherein the received heart rate information includes data that provides accurate information relating to heart rate and heart interbeat interval (IBI) of the animal species under study.

15. The system as defined in claim 14, wherein the data collection unit receives heart rate information from the animal under study when the animal is in a known healthy condition.

16. The system as defined in claim 14, wherein the received heart rate information comprises data sufficient to establish a baseline of heart rate variability data for one or more animals similar to the animal under study who are in a known healthy condition.

17. The system as defined in claim 14, wherein the data analysis unit performs is heart rate variability analysis by determining standard deviation data for variation between heart beats of the received heart rate information, determining high frequency (HF) and low frequency (LF) components of the received heart rate information, and determining a plot of the HF and LF components and identifying quadrants of the plot that correspond to predetermined health condition states.

18. The system as defined in claim 17, wherein the data reporting unit indicates an unhealthy condition of the animal under study if at least one data point of the plot exceeds a predetermined value.

19. The system as defined in claim 17, wherein the health condition report includes a representation of a log-log plot of the HF and LF components.

20. The system as defined in claim 14, wherein the health condition report comprises a health condition signal transmitted over a wireless communication link to a receiving device.

21. The system as defined in claim 20, wherein the receiving device comprises a processing device that communicates with a computer network.

22. The system as defined in claim 20, wherein the receiving device comprises a portable processing device with an integral display that indicates the health condition signal.

23. The system as defined in claim 14, further including:
a wireless communication interface that receives heart rate information from the animal under study over a wireless communication link and provides the heart rate information to the data collection unit.

24. The system as defined in claim 14, further including:
a network processor that receives the heart rate variability analysis and compares the received heart rate information against corresponding heart rate variability data for known healthy condition animal and determines health condition of the animal under study in accordance with the comparison.

25. The system as defined in claim 14, wherein the received heart rate information comprises data that provides accurate information relating to R wave component data of the heart rate information for the animal species under study.

26. The system as defined in claim 14, wherein the health condition report characterization is one of a plurality of characterization categories.

27. The system as defined in claim 26, wherein the characterization categories include at least a category that indicates general health and a category that indicates systemic compromise.

* * * * *